(12) United States Patent
Weiman et al.

(10) Patent No.: US 12,396,866 B2
(45) Date of Patent: Aug. 26, 2025

(54) EXPANDABLE ANTERIOR LUMBAR IMPLANTS

(71) Applicant: GLOBUS MEDICAL, INC., Audubon, PA (US)

(72) Inventors: Mark Weiman, Downingtown, PA (US); Matthew Bakey, Philadelphia, PA (US); Colm Mclaughlin, Glenside, PA (US)

(73) Assignee: Globus Medical, Inc., Audubon, PA (US)

( * ) Notice: Subject to any disclaimer, the term of this patent is extended or adjusted under 35 U.S.C. 154(b) by 153 days.

(21) Appl. No.: 18/475,400

(22) Filed: Sep. 27, 2023

(65) Prior Publication Data
US 2025/0099262 A1   Mar. 27, 2025

(51) Int. Cl.
*A61F 2/44* (2006.01)
*A61F 2/30* (2006.01)

(52) U.S. Cl.
CPC .... *A61F 2/446* (2013.01); *A61F 2002/30537* (2013.01); *A61F 2002/30579* (2013.01)

(58) Field of Classification Search
CPC .. A61F 2/44; A61F 2/446; A61F 2002/30537; A61F 2002/30579
USPC ............................................ 623/17.11–17.16
See application file for complete search history.

(56) References Cited

U.S. PATENT DOCUMENTS

| | | |
|---|---|---|
| 4,349,921 A | 9/1982 | Kuntz |
| 4,599,086 A | 7/1986 | Doty |
| 4,863,476 A | 9/1989 | Shepperd |
| 4,863,477 A | 9/1989 | Monson |
| 5,123,926 A | 6/1992 | Pisharodi |
| 5,290,312 A | 3/1994 | Kojimoto et al. |
| 5,306,310 A | 4/1994 | Siebels |
| 5,375,823 A | 12/1994 | Navas |
| 5,390,683 A | 2/1995 | Pisharodi |
| 5,522,899 A | 6/1996 | Michelson |
| 5,534,030 A | 7/1996 | Navarro et al. |
| 5,554,191 A | 9/1996 | Lahille et al. |
| 5,571,192 A | 11/1996 | Schonhoffer |
| 5,645,596 A | 7/1997 | Kim |
| 5,653,763 A | 8/1997 | Errico et al. |
| 5,665,122 A | 9/1997 | Kambin |
| 5,676,701 A | 10/1997 | Yuan et al. |
| 6,039,761 A | 3/2000 | Li et al. |
| 6,045,579 A | 4/2000 | Hochschuler et al. |
| 6,080,193 A | 6/2000 | Hochschuler et al. |
| 6,099,531 A | 8/2000 | Bonutti |

(Continued)

FOREIGN PATENT DOCUMENTS

| | | |
|---|---|---|
| CA | 2088066 A1 | 1/1992 |
| DE | 4012622 C1 | 7/1991 |

(Continued)

*Primary Examiner* — Jessica Weiss

(57) ABSTRACT

Expandable fusion devices, systems, and methods thereof. The expandable fusion implant may include upper and lower endplates configured to engage adjacent vertebrae and an actuator assembly for expanding the upper and lower endplates to independently control anterior and posterior heights of the implant. The actuator assembly may be operated in two modes: (1) to force the upper and lower endplates apart resulting in parallel expansion; and (2) to increase the anterior height of the implant resulting in an increase in lordotic angle.

17 Claims, 13 Drawing Sheets

(56) References Cited

U.S. PATENT DOCUMENTS

| | | |
|---|---|---|
| 6,126,689 A | 10/2000 | Brett |
| 6,176,882 B1 | 1/2001 | Biedermann et al. |
| 6,258,125 B1 | 7/2001 | Paul et al. |
| 6,554,863 B2 | 4/2003 | Paul et al. |
| 6,558,423 B1 | 5/2003 | Michelson |
| 6,562,074 B2 | 5/2003 | Gerbec et al. |
| 6,576,016 B1 | 6/2003 | Hochschuler et al. |
| 6,641,614 B1 | 11/2003 | Wagner et al. |
| 6,648,917 B2 | 11/2003 | Gerbec et al. |
| 6,666,891 B2 | 12/2003 | Boehm, Jr. et al. |
| 6,692,495 B1 | 2/2004 | Zacouto |
| 6,706,070 B1 | 3/2004 | Wagner et al. |
| 6,752,832 B2 | 6/2004 | Ulrich |
| 6,814,756 B1 | 11/2004 | Michelson |
| 6,830,589 B2 | 12/2004 | Erickson |
| 6,849,093 B2 | 2/2005 | Michelson |
| 6,852,129 B2 | 2/2005 | Gerbec et al. |
| 6,863,673 B2 | 3/2005 | Gerbec et al. |
| 6,881,228 B2 | 4/2005 | Zdeblick et al. |
| 7,018,415 B1 | 3/2006 | McKay |
| 7,070,598 B2 | 7/2006 | Lim et al. |
| 7,204,853 B2 | 4/2007 | Gordon |
| 7,217,291 B2 | 5/2007 | Zucherman et al. |
| 7,282,063 B2 | 10/2007 | Cohen et al. |
| 7,316,714 B2 | 1/2008 | Gordon |
| 7,473,276 B2 | 1/2009 | Aebi et al. |
| 7,547,325 B2 | 6/2009 | Biedermann et al. |
| 7,621,953 B2 | 11/2009 | Braddock, Jr. et al. |
| 7,641,693 B2 | 1/2010 | Gutlin et al. |
| 7,682,396 B2 | 3/2010 | Beaurain et al. |
| 7,749,270 B2 | 7/2010 | Peterman |
| 7,753,958 B2 | 7/2010 | Gordon |
| 7,771,473 B2 | 8/2010 | Thramann |
| 7,780,732 B2 | 8/2010 | Abernathie |
| 7,799,081 B2 | 9/2010 | McKinley |
| 7,815,683 B2 | 10/2010 | Melkent et al. |
| 7,837,734 B2 | 11/2010 | Zucherman et al. |
| 7,875,078 B2 | 1/2011 | Wysocki et al. |
| 7,901,409 B2 | 3/2011 | Canaveral et al. |
| 7,909,869 B2 | 3/2011 | Gordon |
| 7,951,199 B2 | 5/2011 | Miller |
| 7,985,256 B2 | 7/2011 | Grotz et al. |
| 8,062,375 B2 | 11/2011 | Glerum |
| 8,070,813 B2 | 12/2011 | Grotz et al. |
| 8,123,810 B2 | 2/2012 | Gordon |
| 8,137,405 B2 | 3/2012 | Kostuik et al. |
| 8,192,495 B2 | 6/2012 | Simpson et al. |
| 8,303,663 B2 | 11/2012 | Jimenez et al. |
| 8,377,140 B2 | 2/2013 | DeFalco et al. |
| 8,394,129 B2 | 3/2013 | Lopez et al. |
| 8,394,143 B2 | 3/2013 | Grotz et al. |
| 8,435,296 B2 | 5/2013 | Kadaba et al. |
| 8,454,695 B2 | 6/2013 | Grotz et al. |
| 8,647,386 B2 | 2/2014 | Gordon |
| 8,696,751 B2 | 4/2014 | Ashley et al. |
| 8,771,360 B2 | 7/2014 | Jimenez et al. |
| 8,894,710 B2 | 11/2014 | Simpson et al. |
| 8,932,355 B2 | 1/2015 | Grotz et al. |
| 8,940,049 B1 | 1/2015 | JImenez et al. |
| 8,956,413 B2 | 2/2015 | Ashley et al. |
| 8,992,620 B2 | 3/2015 | Ashley et al. |
| 9,028,550 B2 | 5/2015 | Shulock et al. |
| 9,320,610 B2 | 4/2016 | Alheidt et al. |
| 9,358,125 B2 | 6/2016 | JImenez et al. |
| 9,522,070 B2 | 12/2016 | Flower et al. |
| 9,532,883 B2 | 1/2017 | McLuen et al. |
| 9,622,878 B2 | 4/2017 | Grotz |
| 9,962,270 B2 | 5/2018 | Alheidt et al. |
| 10,413,422 B2 | 9/2019 | Flower et al. |
| 10,537,436 B2 | 1/2020 | Maguire et al. |
| 10,575,964 B2 | 3/2020 | Robinson |
| 10,709,569 B2 | 7/2020 | McLaughlin et al. |
| 10,898,344 B2 | 1/2021 | Alheidt et al. |
| 11,497,619 B2 | 11/2022 | Flower et al. |
| 11,602,440 B2 | 3/2023 | Zakelj et al. |
| 2002/0045945 A1 | 4/2002 | Liu |
| 2002/0068976 A1 | 6/2002 | Jackson |
| 2002/0068977 A1 | 6/2002 | Jackson |
| 2003/0176926 A1 | 9/2003 | Boehm et al. |
| 2004/0030387 A1 | 2/2004 | Landry et al. |
| 2004/0049271 A1 | 3/2004 | Biedermann |
| 2004/0054412 A1 | 3/2004 | Gerbec et al. |
| 2004/0087947 A1 | 5/2004 | Lim et al. |
| 2004/0153065 A1 | 8/2004 | Lim |
| 2005/0021041 A1 | 1/2005 | Michelson |
| 2005/0021145 A1 | 1/2005 | de Villiers et al. |
| 2005/0033432 A1 | 2/2005 | Gordon |
| 2005/0080422 A1 | 4/2005 | Otte et al. |
| 2005/0113916 A1 | 5/2005 | Branch |
| 2005/0149188 A1 | 7/2005 | Cook |
| 2005/0171541 A1 | 8/2005 | Boehm |
| 2005/0251258 A1 | 11/2005 | Jackson |
| 2005/0273171 A1 | 12/2005 | Gordon |
| 2005/0273174 A1 | 12/2005 | Gordon |
| 2005/0278026 A1 | 12/2005 | Gordon |
| 2005/0283244 A1 | 12/2005 | Gordon |
| 2005/0283245 A1 | 12/2005 | Gordon |
| 2006/0004453 A1 | 1/2006 | Bartish, Jr. et al. |
| 2006/0015184 A1 | 1/2006 | Winterbottom et al. |
| 2006/0058878 A1 | 3/2006 | Michelson |
| 2006/0084986 A1 | 4/2006 | Grinberg et al. |
| 2006/0122701 A1 | 6/2006 | Kister |
| 2006/0129244 A1 | 6/2006 | Ensign |
| 2006/0142859 A1 | 6/2006 | Mcluen |
| 2006/0149385 A1 | 7/2006 | Mckay |
| 2006/0195192 A1 | 8/2006 | Gordon et al. |
| 2006/0229729 A1 | 10/2006 | Gordon |
| 2006/0241770 A1 | 10/2006 | Rhoda et al. |
| 2006/0253201 A1 | 11/2006 | Mcluen |
| 2007/0043442 A1 | 2/2007 | Abernathie |
| 2007/0050030 A1 | 3/2007 | Kim |
| 2007/0050032 A1 | 3/2007 | Gittings et al. |
| 2007/0055377 A1 | 3/2007 | Hanson et al. |
| 2007/0191951 A1 | 8/2007 | Branch |
| 2007/0255415 A1 | 11/2007 | Edie et al. |
| 2007/0270963 A1 | 11/2007 | Melkent et al. |
| 2007/0270968 A1 | 11/2007 | Baynham |
| 2008/0021559 A1 | 1/2008 | Thramann |
| 2008/0065222 A1 | 3/2008 | Hamada |
| 2008/0114467 A1 | 5/2008 | Capote et al. |
| 2008/0140207 A1 | 6/2008 | Olmos et al. |
| 2008/0147194 A1 | 6/2008 | Grotz et al. |
| 2008/0161933 A1 | 7/2008 | Grotz et al. |
| 2008/0167657 A1 | 7/2008 | Greenhalgh |
| 2008/0183204 A1 | 7/2008 | Greenhalgh et al. |
| 2008/0221694 A1 | 9/2008 | Warnick et al. |
| 2008/0275455 A1 | 11/2008 | Berry et al. |
| 2008/0281346 A1 | 11/2008 | Greenhalgh et al. |
| 2008/0288073 A1 | 11/2008 | Renganath et al. |
| 2008/0300598 A1 | 12/2008 | Barreiro et al. |
| 2008/0306488 A1 | 12/2008 | Altarac et al. |
| 2008/0319487 A1 | 12/2008 | Fielding et al. |
| 2008/0319549 A1 | 12/2008 | Greenhalgh et al. |
| 2009/0024217 A1 | 1/2009 | Levy et al. |
| 2009/0062833 A1 | 3/2009 | Song |
| 2009/0076616 A1 | 3/2009 | Duggal et al. |
| 2009/0125062 A1 | 5/2009 | Arnin |
| 2009/0149956 A1 | 6/2009 | Greenhalgh et al. |
| 2009/0149959 A1 | 6/2009 | Conner et al. |
| 2009/0204218 A1 | 8/2009 | Richelsoph |
| 2009/0222100 A1 | 9/2009 | Cipoletti et al. |
| 2009/0240334 A1 | 9/2009 | Richelsoph |
| 2009/0270989 A1 | 10/2009 | Conner et al. |
| 2009/0281628 A1 | 11/2009 | Oglaza et al. |
| 2009/0292361 A1 | 11/2009 | Lopez |
| 2009/0299478 A1 | 12/2009 | Carls et al. |
| 2009/0312763 A1 | 12/2009 | McCormack |
| 2010/0049324 A1 | 2/2010 | Valdevit |
| 2010/0070041 A1 | 3/2010 | Peterman |
| 2010/0082109 A1 | 4/2010 | Greenhalgh et al. |
| 2010/0145455 A1 | 6/2010 | Simpson et al. |
| 2010/0179657 A1 | 7/2010 | Greenhalgh et al. |
| 2010/0211176 A1 | 8/2010 | Greenhalgh |
| 2010/0222816 A1 | 9/2010 | Gabelberger et al. |

(56) References Cited

U.S. PATENT DOCUMENTS

| | | |
|---|---|---|
| 2010/0286783 A1 | 11/2010 | Lechmann et al. |
| 2011/0035011 A1 | 2/2011 | Cain |
| 2011/0093074 A1 | 4/2011 | Glerum et al. |
| 2011/0160861 A1 | 6/2011 | Jimenez et al. |
| 2011/0172774 A1 | 7/2011 | Varela |
| 2011/0276142 A1 | 11/2011 | Niemiec et al. |
| 2011/0301713 A1 | 12/2011 | Theofilos |
| 2011/0319997 A1 | 12/2011 | Glerum et al. |
| 2012/0035729 A1 | 2/2012 | Glerum et al. |
| 2012/0059470 A1 | 3/2012 | Weiman |
| 2012/0059472 A1 | 3/2012 | Weiman |
| 2012/0109308 A1 | 5/2012 | Lechmann et al. |
| 2012/0130496 A1 | 5/2012 | Duffield et al. |
| 2012/0165945 A1 | 6/2012 | Hansell et al. |
| 2012/0185049 A1 | 7/2012 | Varela |
| 2012/0209386 A1 | 8/2012 | Triplett et al. |
| 2012/0215313 A1 | 8/2012 | Saidha et al. |
| 2012/0226357 A1 | 9/2012 | Varela |
| 2012/0265309 A1 | 10/2012 | Glerum et al. |
| 2012/0277861 A1 | 11/2012 | Steele et al. |
| 2012/0277870 A1 | 11/2012 | Wolters et al. |
| 2012/0323329 A1 | 12/2012 | Jimenez et al. |
| 2012/0330426 A1 | 12/2012 | McLaughlin et al. |
| 2013/0023993 A1 | 1/2013 | Weiman |
| 2013/0023994 A1 | 1/2013 | Glerum |
| 2013/0158663 A1 | 6/2013 | Miller et al. |
| 2013/0158664 A1* | 6/2013 | Palmatier ............... A61F 2/4425 623/17.16 |
| 2013/0158669 A1 | 6/2013 | Sungarian et al. |
| 2013/0197647 A1 | 8/2013 | Wolters et al. |
| 2013/0211526 A1 | 8/2013 | Alheidt et al. |
| 2013/0274883 A1 | 10/2013 | McLuen et al. |
| 2014/0067071 A1 | 3/2014 | Weiman et al. |
| 2014/0088714 A1 | 3/2014 | Miller et al. |
| 2014/0163683 A1* | 6/2014 | Seifert ............... A61F 2/4455 623/17.15 |
| 2015/0066145 A1 | 3/2015 | Rogers et al. |
| 2015/0088258 A1 | 3/2015 | Jimenez et al. |
| 2015/0134064 A1 | 5/2015 | Grotz et al. |
| 2015/0216676 A1 | 8/2015 | Shulock et al. |
| 2015/0289988 A1 | 10/2015 | Ashley et al. |
| 2015/0374508 A1 | 12/2015 | Sandul |
| 2016/0151168 A1* | 6/2016 | Weiman ............... A61F 2/44 623/17.16 |
| 2016/0166396 A1* | 6/2016 | McClintock ............ A61F 2/446 623/17.16 |
| 2016/0324654 A1 | 11/2016 | Loebl et al. |
| 2017/0100258 A1 | 4/2017 | Jimenez et al. |
| 2017/0119543 A1 | 5/2017 | Dietzel et al. |
| 2022/0133493 A1 | 5/2022 | Josse et al. |
| 2022/0304823 A1 | 9/2022 | Melchor |
| 2022/0313450 A1 | 10/2022 | Donohoe et al. |
| 2022/0387190 A1 | 12/2022 | Klausman et al. |
| 2022/0395379 A1 | 12/2022 | Ries et al. |
| 2023/0181329 A1 | 6/2023 | Zakelj |

FOREIGN PATENT DOCUMENTS

| | | |
|---|---|---|
| DE | 4327054 C1 | 4/1995 |
| EP | 0576379 B1 | 6/1993 |
| EP | 0610837 B1 | 7/1994 |
| EP | 3111896 A1 | 1/2017 |
| FR | 2794968 A1 | 12/2000 |
| JP | 2000-513263 A | 10/2000 |
| KR | 200290058 Y1 | 9/2002 |
| SU | 1424826 A1 | 9/1988 |
| WO | 9201428 A1 | 2/1992 |
| WO | 9525485 A1 | 9/1995 |
| WO | 1999042062 A1 | 8/1999 |
| WO | 1999066867 A1 | 12/1999 |
| WO | 2002045625 A1 | 6/2002 |
| WO | 2004019829 A1 | 3/2004 |
| WO | 2004069033 A2 | 8/2004 |
| WO | 2006045094 A2 | 4/2006 |
| WO | 2006047587 A2 | 5/2006 |
| WO | 2006113080 A2 | 10/2006 |
| WO | 2008044057 A1 | 4/2008 |
| WO | 2008134515 A1 | 11/2008 |
| WO | 2009114381 A1 | 9/2009 |
| WO | 2010103344 A1 | 9/2010 |
| WO | 2012031267 A1 | 3/2012 |
| WO | 2015009793 A1 | 1/2015 |

* cited by examiner

EXPANDABLE ANTERIOR LUMBAR IMPLANTS

FIELD OF THE INVENTION

The present disclosure generally relates to devices and methods for promoting an intervertebral fusion, and more particularly relates to expandable fusion devices capable of being inserted between adjacent vertebrae to facilitate the fusion process and related systems and methods.

BACKGROUND OF THE INVENTION

A common procedure for handling pain associated with intervertebral discs that have become degenerated due to various factors, such as trauma or aging, is the use of intervertebral fusion devices for fusing one or more adjacent vertebral bodies. Generally, to fuse the adjacent vertebral bodies, the intervertebral disc is first partially or fully removed. An intervertebral fusion device is then inserted between neighboring vertebrae to maintain normal disc spacing and restore spinal stability, thereby facilitating an intervertebral fusion.

There are a number of fusion devices and methodologies for accomplishing the intervertebral fusion. These may include solid bone implants, fusion devices which include a cage or other implant mechanism, which may be packed with bone and/or bone growth inducing substances, and expandable implants. The expandable implants may be inserted into the intervertebral disc space at a minimized height, and then expanded to restore height loss in the disc space.

There are drawbacks, however, with existing expandable implants including excessive impaction during insertion, visual obstruction, and imperfect matching with patient's lordosis due to discrete increments in lordotic angulation. As such, there exists a need for fusion devices capable of providing distraction as well as achieving optimal height restoration and changes in lordotic angulation independently from its expansion.

SUMMARY OF THE INVENTION

To meet this and other needs, implants, systems, and methods for performing intervertebral fusion and spine stabilization are provided. In particular, expandable intervertebral implants, for example, for anterior spinal surgery may be used to treat a variety of patient indications. The expandable implants are configured to be inserted into the intervertebral disc space at a minimized height, and then expanded axially to restore normal spinal alignment and distribute the load across the vertebral endplates. The implant may provide distraction as well as achieving optimal height restoration. The implant may also change in lordotic angulation independently from its expansion.

According to one embodiment, an expandable implant includes an upper endplate and a lower endplate configured to engage adjacent vertebrae and an actuator assembly for expanding the upper and lower endplates to independently control anterior and posterior heights of the implant. The actuator assembly includes a moveable anterior actuator, a moveable posterior actuator, and a stationary posterior actuator positioned between the upper and lower endplates. An actuator screw threads into an anterior actuator nut located in the moveable anterior actuator and a posterior actuator nut located in the stationary posterior actuator. The actuator screw threads through the moveable posterior actuator to translate the posterior actuator. When the actuator screw and anterior actuator nut are turned together, the moveable posterior actuator moves toward the stationary posterior actuator, forcing the upper and lower endplates apart resulting in parallel expansion. When only the anterior actuator nut is turned, the moveable anterior actuator moves alone to increase the anterior height, resulting in an increase in lordotic angle.

The expandable implant may include one or more of the following features. The upper and lower endplates may define a plurality of ramps configured to mate with corresponding ramps on the anterior and posterior actuators. The ramps on the upper and lower endplates may include female T-slots. The ramps on the anterior and posterior actuators may include male protrusions with point contact pivoting ramps, facilitating pivoting or rotational movement. The moveable anterior actuator may include a laterally extending body with an enlarged central portion defining a non-threaded bore and free ends defining an irregular cross-sectional shape with a pair of male ramps extending from each end of the anterior actuator. The moveable posterior actuator may include a laterally extending body defining a threaded bore with a flat anterior face and an opposite posterior face defining point contact pivoting ramps configured to interface with the corresponding ramps of the upper and lower endplates. The stationary posterior actuator may include a laterally extending body defining a non-threaded bore with an anterior face defining point contact pivoting ramps configured to interface with the corresponding ramps of the upper and lower endplates. The actuator screw may include a shaft having a single type of thread profile along its length and a reduced diameter at its distal end to thread into the posterior actuator nut. The single type of thread profile achieves both parallel and lordotic expansion.

According to another embodiment, an expandable implant includes an upper endplate and a lower endplate configured to engage adjacent vertebrae and an actuator assembly for expanding the upper and lower endplates to independently control anterior and posterior heights of the implant. The actuator assembly includes a moveable anterior actuator securing a plurality of anterior pivot ramps, a moveable posterior actuator and a stationary posterior actuator engaged with upper and lower posterior pivot ramps, and an actuator screw threaded into an anterior actuator nut located in the moveable anterior actuator and a posterior actuator nut located in the stationary posterior actuator. The actuator screw threads through the moveable posterior actuator to translate the posterior actuator. When the actuator screw and the anterior actuator nut are turned together, the moveable posterior actuator moves toward the stationary posterior actuator, forcing the posterior pivot ramps outward resulting in parallel expansion of the upper and lower endplates. When only the anterior actuator nut is turned, the moveable anterior actuator moves alone to increase the anterior height, resulting in an increase in lordotic angle.

The expandable implant may include one or more of the following features. The upper and lower endplates may define a plurality of ramps configured to mate with corresponding ramps on the anterior and posterior pivot ramps. Each anterior pivot ramp may have a ring received on the moveable anterior actuator and a foot with a sliding surface configured to mate with respective ramps on the upper and lower endplates. The foot may be a male projection extending from one side of the ring, and the ramp on the upper and lower endplates may be a female recess configured to receive the male projection of the foot. The moveable anterior actuator may include a laterally extending body with an enlarged central portion defining a non-threaded bore and free ends defining cylindrical ends. Each anterior pivot ramp may have a smooth inner surface to allow each anterior pivot ramp to rotate on the cylindrical ends of the moveable anterior actuator. The posterior pivot ramps may be separated into left and right sections positioned on opposite sides of the actuator screw. The posterior pivot ramps may include a lateral extending body with a bell-shaped cross section having a tapered end and flared end. The flared end of the posterior pivot ramps may include a lateral rib having a circular cross section configured to pivot in a corresponding channel in the upper and lower endplates.

According to another embodiment, a method of spinal fixation includes: inserting an expandable intervertebral implant into a disc space between adjacent vertebrae, the expandable implant comprising upper and lower endplates and an actuator assembly including a moveable anterior actuator, a moveable posterior actuator, and a stationary posterior actuator positioned between the upper and lower endplates, an actuator screw threads into an anterior actuator nut located in the moveable anterior actuator and a posterior actuator nut located in the stationary posterior actuator, the actuator screw threads through the moveable posterior actuator to translate the posterior actuator; and expanding the implant in height by (1) rotating the actuator screw and anterior actuator nut together to move the moveable posterior actuator toward the stationary posterior actuator, thereby forcing the upper and lower endplates apart resulting in parallel expansion; or (2) rotating only the anterior actuator nut to move the moveable anterior actuator alone to increase the anterior height, resulting in an increase in lordotic angle. The method may also include inserting bone anchors through sockets in the upper and lower endplates and into the adjacent vertebrae, and rotating blocking screws in the upper and lower endplates to cover the bone anchors and prevent the bone anchors backing out.

According to yet another embodiment, a kit may include a plurality of expandable implants of different sizes and configurations, fasteners or anchors, k-wires, and other components for performing the procedure. The kit may further include one or more devices suitable for installing and/or removing the implants, such as insertion devices or drivers, expansion instruments, removal devices, and other tools and devices which may be suitable for surgery.

BRIEF DESCRIPTION OF THE DRAWINGS

The present embodiments will become more fully understood from the detailed description and the accompanying drawings, wherein.

DETAILED DESCRIPTION

Figure 1A:
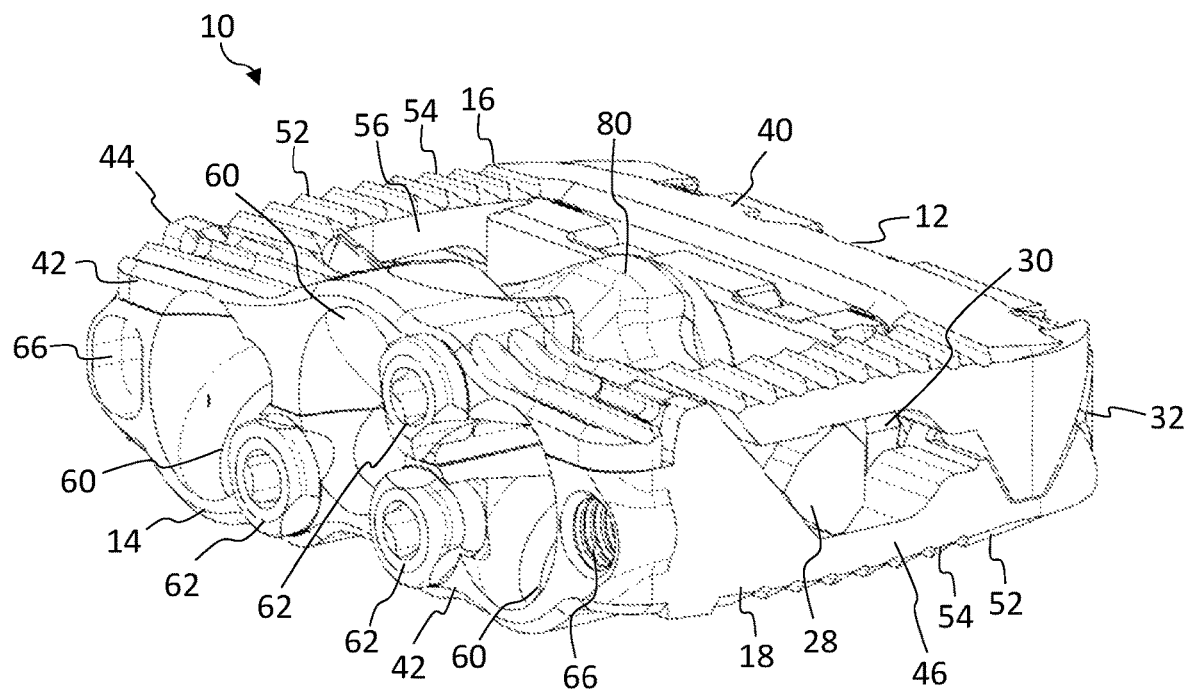
FIGS. 1A-1B illustrate perspective and side views, respectively, of an expandable implant in a collapsed position according to one embodiment.

Embodiments of the disclosure are generally directed to devices, systems, and methods for intervertebral fusion and spine stabilization. Specifically, expandable implants are configured to be inserted into the intervertebral disc space at a minimized height, and then expanded axially to restore normal spinal alignment and distribute the load across the vertebral endplates. The implant may provide distraction as well as achieving optimal height restoration. The implant may also change in lordotic angulation independently from its expansion.

A spinal fusion is typically employed to eliminate pain caused by motion of degenerated disc material. Upon successful fusion, a fusion device becomes permanently fixed within the intervertebral disc space. The expandable fusion device may be positioned between adjacent vertebral bodies in a collapsed position. The expandable fusion device is configured to expand in height to restore height loss in the disc space. The fusion device engages the endplates of the adjacent vertebral bodies and, in the installed position, maintains desired intervertebral disc spacing and restores spinal stability, thereby facilitating the intervertebral fusion.

Minimally invasive surgery (MIS) may be used to preserve muscular anatomy by only causing disruption where necessary. The benefit of the MIS surgical approach is that it can reduce post-operative pain and improve recovery time for patients. In one embodiment, the expandable fusion device can be configured to be placed down an endoscopic tube and into the surgical target site. By way of example, the surgical site may be an intervertebral disc space situated between two adjacent vertebrae. Although particularly suited for use in an anterior lumbar interbody fusion (ALIF), it will be readily appreciated by those skilled in the art that the implant may be employed in any number of suitable orthopedic approaches and procedures, such as direct lateral where coronal deformity is encountered. Other approaches may include but are not limited to posterior, lateral, anterolateral, posterolateral, or transforaminal approaches to the lumbar spine, cervical spine, or thoracic spine, as well as any non-spine application, such as treatment of bone fractures and the like. The terms implant, interbody, interbody implant, fusion device, spacer, and expandable device may be used interchangeably herein.

Components of all of the devices disclosed herein may be manufactured of any suitable materials including metals (e.g., titanium), metal alloys (e.g., stainless steel, cobalt-chromium, and titanium alloys), ceramics, plastics, plastic composites, or polymeric materials (e.g., polyether ether ketone (PEEK), polyphenylene sulfone (PPSU), polysulfone (PSU), polycarbonate (PC), polyetherimide (PEI), polypropylene (PP), polyacetals, or mixtures or co-polymers thereof), and/or combinations thereof. In some embodiments, the devices may include radiolucent and/or radiopaque materials. The components can also be machined and/or manufactured using any suitable techniques (e.g., 3D printing).

Turning now to the drawing, where like reference numerals refer to like elements, FIG. 1A-7 illustrate an expandable fusion device or implant 10 according to one embodiment. The expandable implant 10 extends along a central longitudinal axis A between a front end or posterior end 12 and a rear end or anterior end 14 of the device 10. The implant 10 includes upper and lower endplates 16, 18 configured to engage adjacent vertebrae, which define a height of the implant 10. The implant 10 includes an actuator assembly 20 configured for expanding the upper and lower endplates 16, 18. The actuator assembly 20 includes a single actuator screw 22 threaded into anterior and posterior actuator ramps 28, 30 to independently control the anterior and posterior height of the implant 10.

The implant 10 may include three separate actuators 28, 30, 32 positioned between the upper and lower endplates 16, 18: a moveable anterior actuator 28, a moveable posterior actuator 30, and a stationary posterior actuator 32. One end of the actuator screw 22 threads into an anterior actuator nut 24 located in the anterior actuator 28 and the opposite end of the actuator screw 22 threads into a posterior actuator nut 26 affixed to the stationary posterior actuator 32. The actuator screw 22 threads through the moveable posterior actuator 30 to translate the posterior actuator 30 along longitudinal axis A. When the actuator screw 22 and anterior actuator nut 24 are turned together, the moveable posterior actuator 30 moves toward the stationary posterior actuator 32, forcing the upper and lower endplates 16, 18 apart resulting in parallel expansion. When only the anterior actuator nut 24 is turned, the moveable anterior actuator 28 moves alone to increase the anterior height, resulting in an increase in lordotic angle.

Figure 1B:
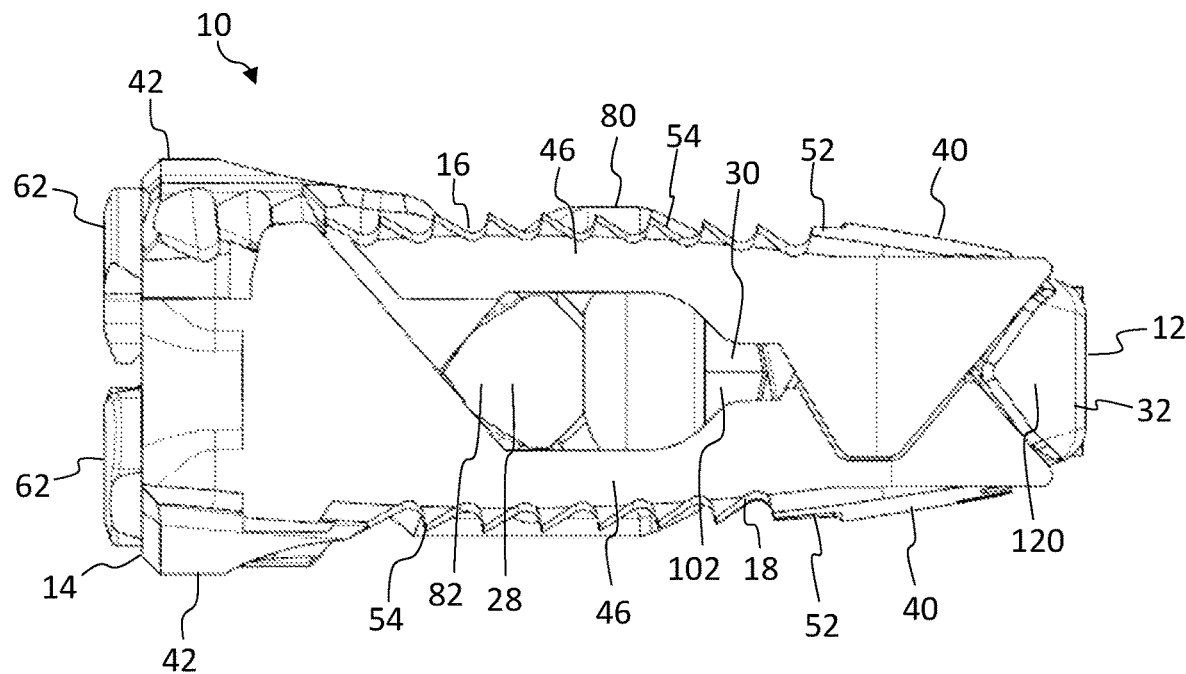
Figure 2A:
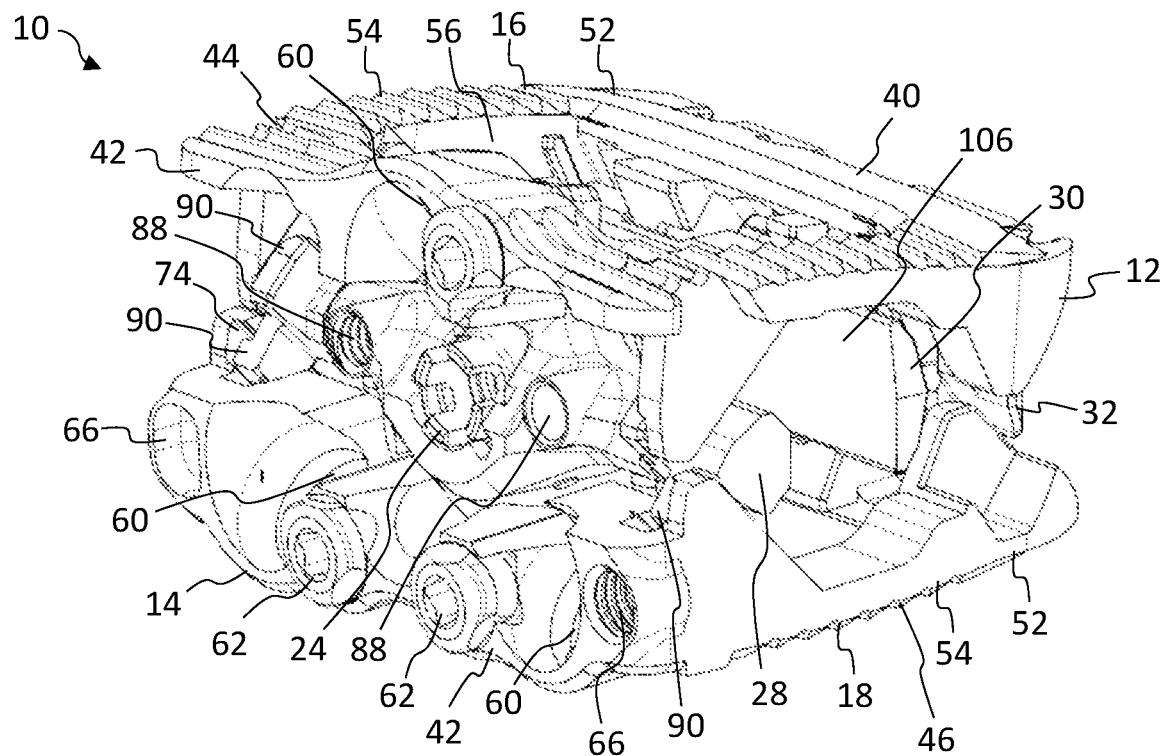
FIGS. 2A-2B illustrate perspective and side views, respectively, of the expandable implant in a fully expanded position according to one embodiment.
Figure 2B:
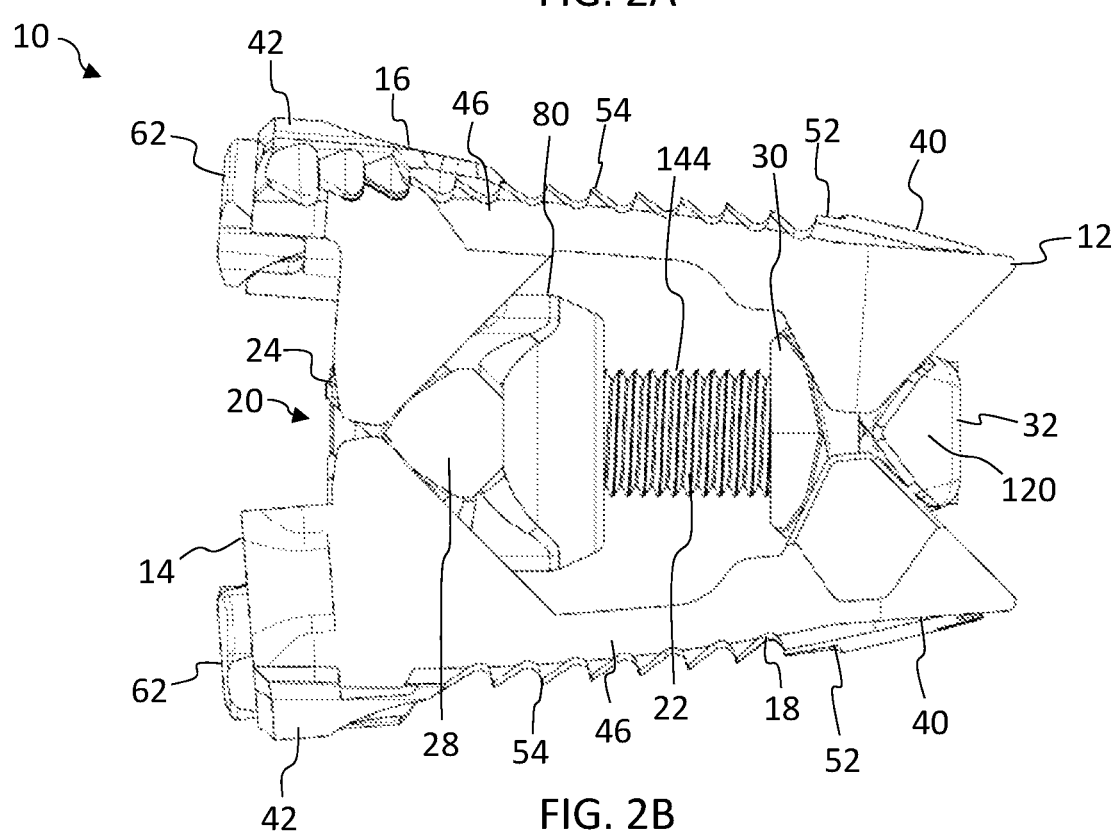
Figure 3A:
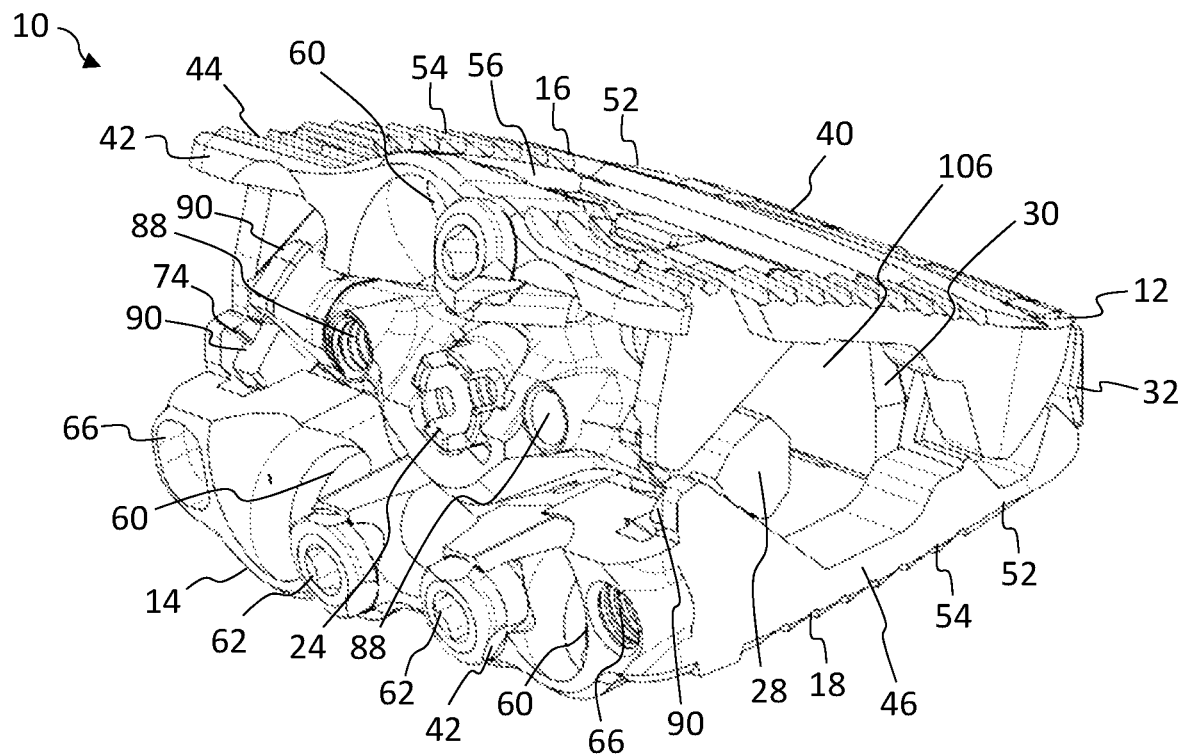
FIGS. 3A-3B illustrate perspective and side views, respectively, of the expandable implant in an expanded position with the anterior and posterior height of the implant independently controlled according to one embodiment.
Figure 3B:
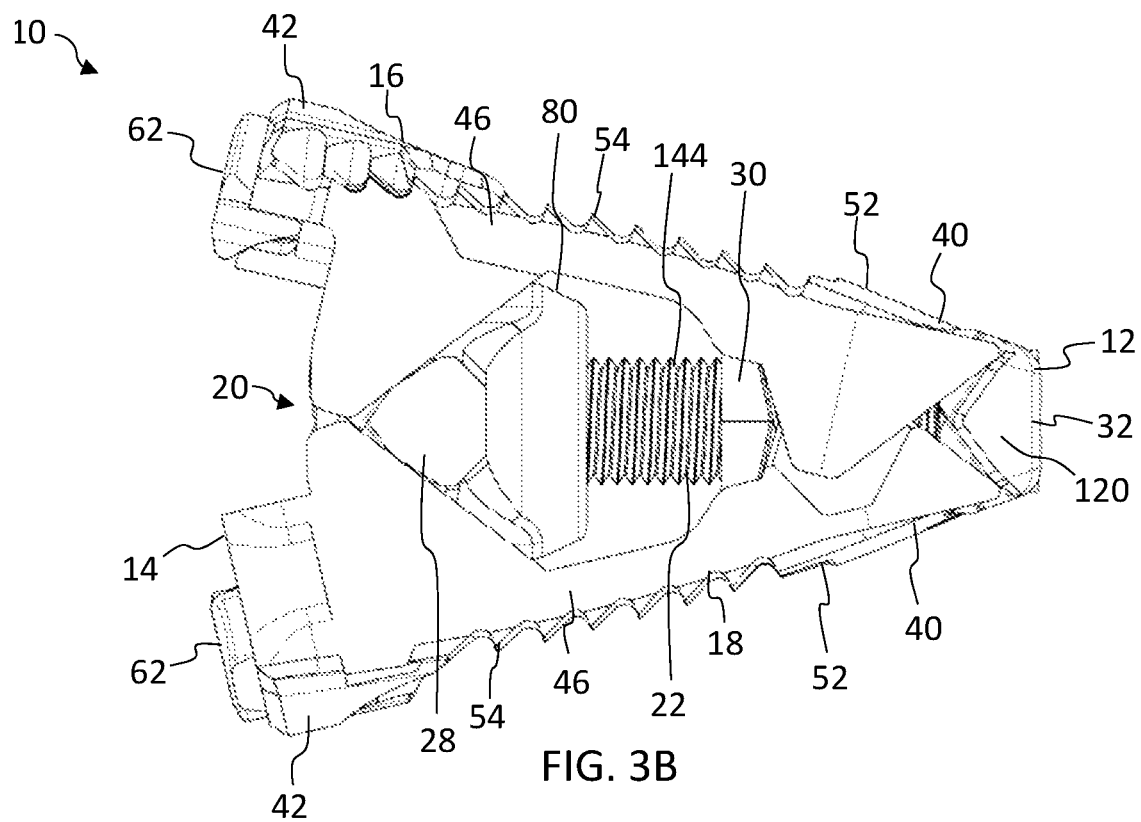
Figure 4:
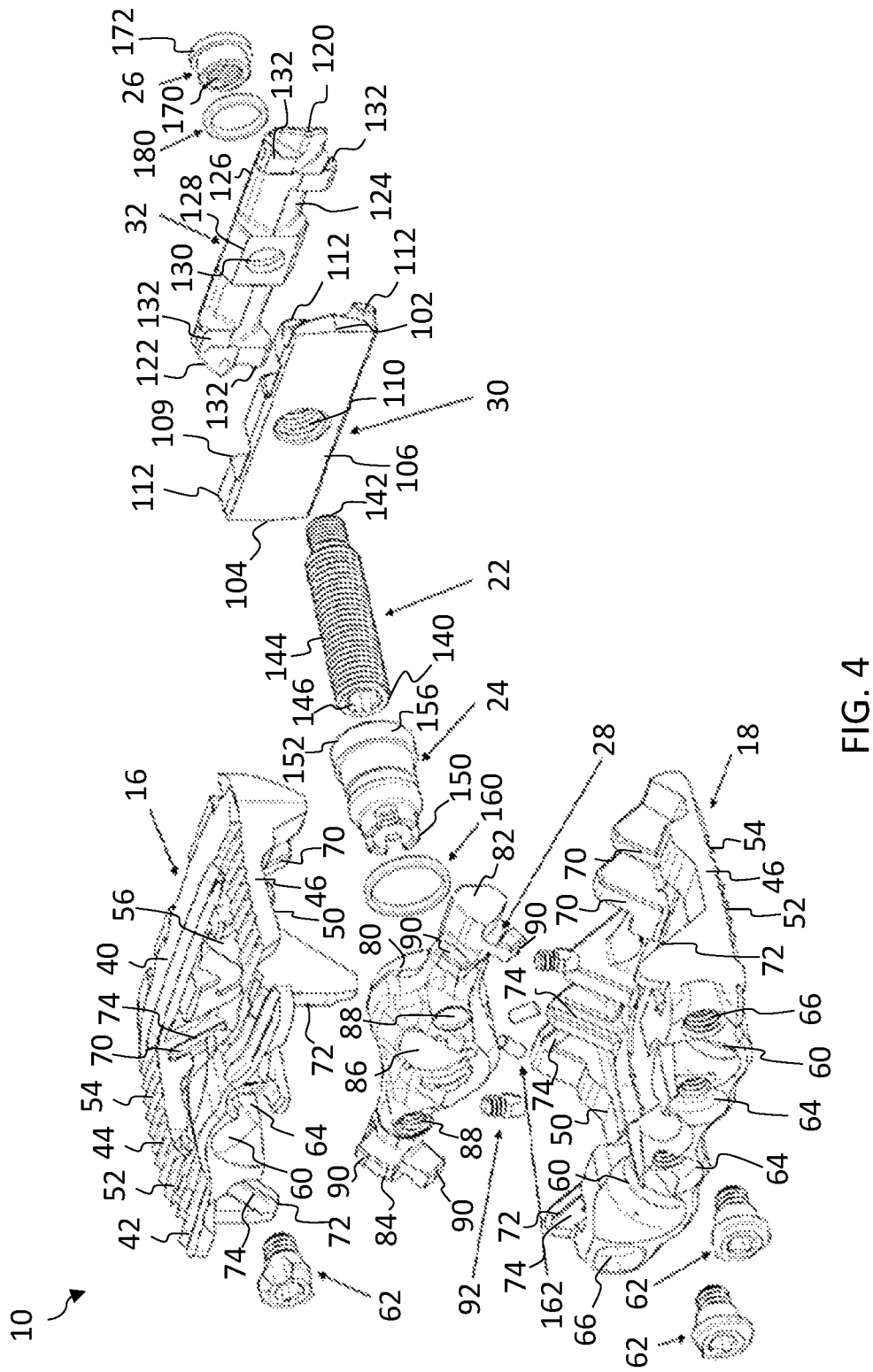
FIG. 4 illustrates an exploded view of the expandable implant according to one embodiment.

The implant 10 is configured to be inserted into the disc space in a collapsed configuration. FIGS. 1A-1B show the implant 10 in the collapsed configuration. Once inserted into the disc space, the implant 10 is expanded in height to an expanded configuration to precisely restore spinal alignment and distribute load across the vertebral endplates. FIGS. 2A-2B show the implant 10 in a fully expanded configuration. FIGS. 3A-3B show the implant 10 in an expanded configuration where the anterior and posterior heights are independently adjustable to a desired lordotic profile. In this manner, the height is adjustable to restore height loss in the disc space and lordotic angulation. It should be understood that reference to the front and rear ends and anterior and posterior heights are described with respect to the direction of placement into an intervertebral disc space with the front of the expandable fusion device 10 placed into the disc space first, followed by the rear of the expandable fusion device 10, and then expanding the endplates 16, 18 in height and/or lordosis. These and other directional terms may be used herein for descriptive purposes and do not limit the orientation(s) in which the devices may be used.

Each endplate 16, 18 may include a front or posterior rail 40 and a rear or anterior rail 42 extending between opposed side rails 44, 46. The rails 40-46 define an inner face 50 and an opposite outer face 52. The inner face 50 may be configured to mate with the respective actuators 28, 30, 32 and the outer face 52 may be configured to contact adjacent vertebrae. The outer face 52 of each endplate 16, 18 may include a plurality of teeth 54 or other friction increasing elements, such as ridges, roughened surfaces, keels, gripping or purchasing projections configured to retain the device 10 in the disc space. The endplates 16, 18 may be 3D printed using additive manufacturing. In this manner, the outer face 52 may be created with teeth and/or surface texturing that can better facilitate bony on-growth. Each endplate 16, 18 may define a vertical window or through passage 56, thereby defining a central graft chamber within the implant 10. The window or through passage 56 allows graft material or other therapeutically beneficial material to be packed into or grow through the implant 10.

The implant 10 may be secured to the adjacent vertebrae with one or more anchors or fixation screws (not shown). For example, the anterior rail 42 may define at least one anchor socket 60 configured for receiving the anchor or fixation screw therethrough and into the adjacent vertebra. In the embodiment shown, three sockets 60 for receiving three respective anchors or screws are provided in the upper and lower endplates 16, 18: one socket 60 pointed upward into the superior vertebra and two sockets 60 pointed downward into the inferior vertebra. The sockets 60 may be surrounded by a hemispherical protrusion such that the anchors or screws may be angled into the adjacent vertebrae. In one embodiment, the bone screws may be polyaxial screws, and sockets 60 correspondingly shaped, such that the polyaxial screws may be inserted at optimal angles with respect to implant 10. In another embodiment, the anchor may be a curved, t-shaped shim-type anchor with sharp edges to penetrate bone. Examples of bone screws and anchors are further described in in U.S. Pat. No. 11,554,023, which is incorporated by reference herein in its entirety for all purposes. Although a given configuration of sockets 60 is shown, it will be appreciated that the sockets 60 may be present in any suitable number and configuration for fixation. In the alternative, the sockets 60 may be omitted to provide a standalone device.

Cam style blocking screws 62 may be used to block the anchors or fixation screws from backing out after being inserted. The anterior rail 42 may define a blocking screw hole 64 positioned next to each respective socket 60. The blocking screw holes 64 may be internally threaded to receive the respective threaded blocking screws 62. In one embodiment, three blocking screws 62 thread into the endplates 16, 18 to secure the anchors or fixation screws in the three respective sockets 60. The blocking screws 62 may have an enlarged head with a drive recess and a threaded shaft. When the blocking screws 62 are rotated and engaged, a portion of the enlarged head covers the respective anchors or fixation screws, thereby preventing migration of the installed anchors or fixation screws.

Figure 5A:
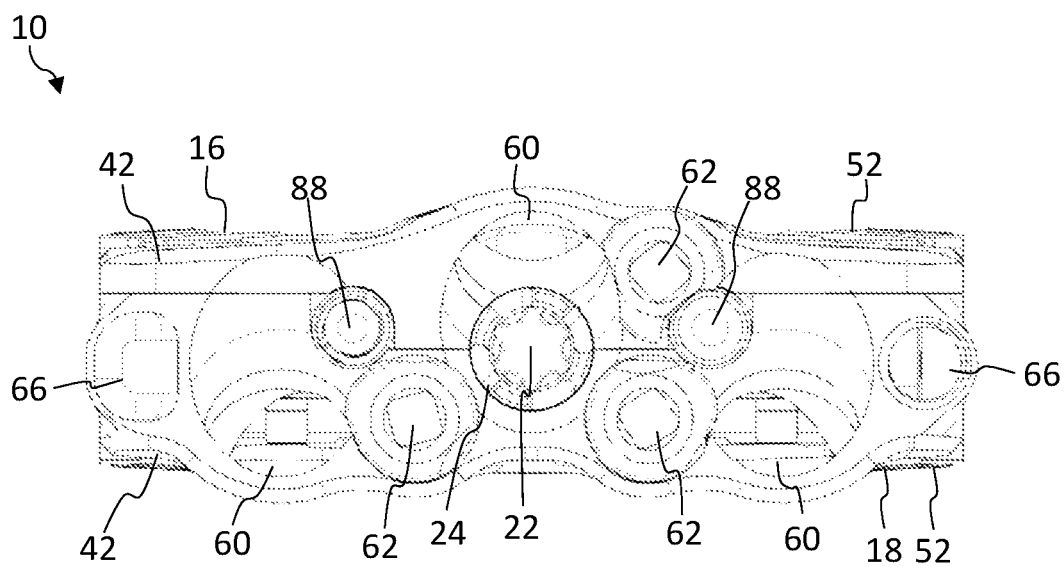
FIGS. 5A-5B illustrate anterior or rear views of the expandable implant in the collapsed and fully expanded positions, respectively, according to one embodiment.
Figure 5B:
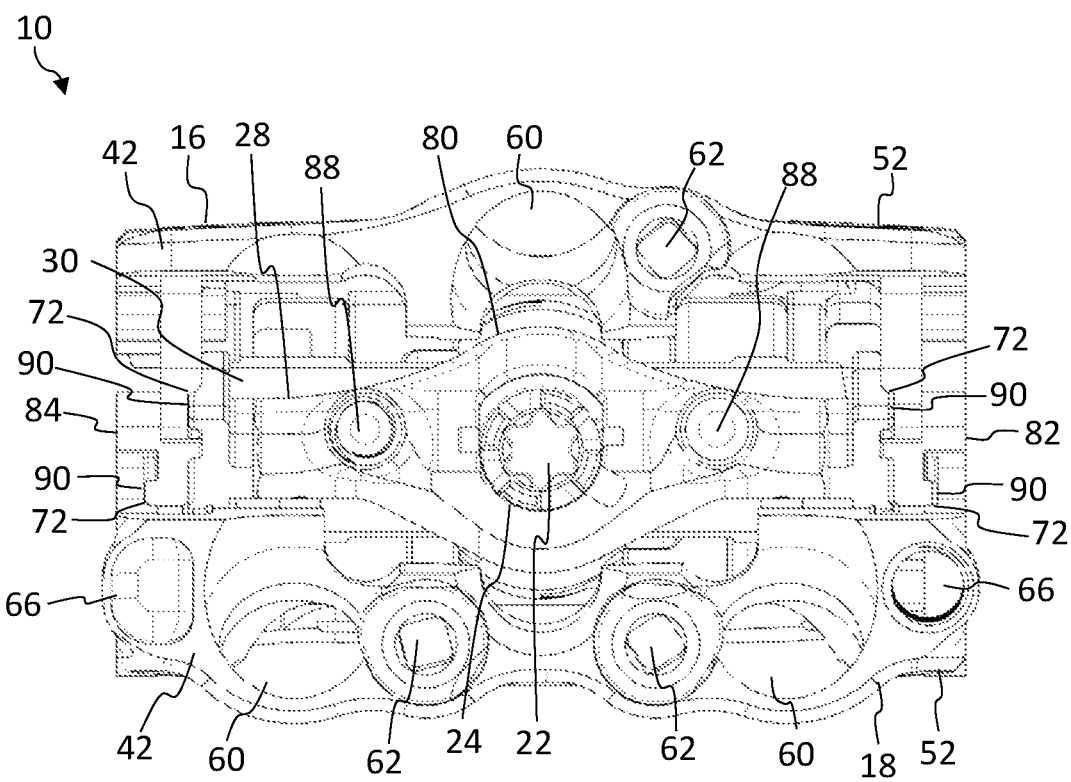

As best seen in FIG. 5A, the implant 10 may include one or more recesses or openings 66 for receiving an instrument, such as an insertion and/or expansion instrument. The anterior rail 42 of the lower endplate 18 may define a first opening 66 on one lateral side and a second opening 66 on the opposite side of the lower endplate 18 configured to be retained by an insertion instrument. For example, the first opening 66 may be a threaded cylindrical opening configured to receive a threaded portion of the inserter instrument and the second opening 66 may be a non-threaded non-cylindrical recess configured to receive a non-threaded portion of the inserter instrument. It will be appreciated that the implant 10 may connect with an insertion and/or expansion instrument in any suitable manner.

The inner face 50 of each endplate 16, 18 may include one or more ramps 70, 72 configured to mate with the respective actuators 28, 30, 32, thereby causing endplates 16, 18 to separate apart. For example, the endplates 16, 18 may define posterior ramps 70 along the inner face 50 of the posterior rail 50 and anterior ramps 72 along the inner face 50 of the side rails 44, 46. The ramps 70, 72 may include ramped surfaces, angled surfaces, or inclined planes with a given gradient or angle of slope. The ramps 70, 72 may have generally straight ramped surfaces, may be curved, or may be configured in any suitable manner for slidable interface between the components. The ramps 70, 72 may define male or female slide ramps configured to mate with corresponding ramps 90, 112, 132 on the actuators 28, 30, 32. In one embodiment, the ramps 70, 72 on endplates 16, 18 include female ramps with grooves or slots 74 defined therein, such as T-slots. The groove or slots 74 may be configured to receive a portion of point contact pivoting ramps 90, 112, 132 of the actuators 28, 30, 32. As the anterior and/or posterior actuators 28, 30, 32 translate and slide against the ramps 70, 72 of the endplates 16, 18, the movement provides for expansion or contraction of the implant 10. The expansion may include the ability to individually adjust the anterior and/or posterior heights of the implant 10.

The actuator assembly 20 includes moveable anterior actuator 28 positioned between the upper and lower endplates 16, 18, thereby providing anterior expansion to the implant 10. The moveable anterior actuator 28 includes a laterally extending body with an enlarged central portion 80. The anterior actuator 28 extends from a first free end 82 to a second free end 84. The first and second ends 82, 84 may define an irregular cross-sectional shape, such as a polygon with facets and rounded corners. The first and second free ends 82, 84 are receivable between the side rails 44, 46 toward the anterior end 14 of the upper and lower endplate 16, 18 and the enlarged central portion 80 is positionable through the graft window 56 of the upper and lower endplates 16, 18 when in the collapsed configuration. The enlarged central portion 80 defines a central non-threaded bore 86 sized and dimensioned to receive the anterior actuator nut 24. The central axis of bore 86 may be aligned with the central longitudinal axis A of the implant 10. Additional recesses or bores 88 may be provided through the anterior actuator 28. For example, a first threaded bore 88 may be provided on one side of the central bore 86 and a second non-threaded bore 88 may be provided on the opposite side of the central bore 86. Recesses or bores 88 may be used to attach an instrument, such as an insertion and/or expansion instrument.

The moveable anterior actuator 28 includes one or more ramps 90 configured to mate with corresponding anterior ramps 72 on the endplates 16, 18. The ramps 90 may include two point contact pivoting ramp surfaces incorporated into each side of the anterior actuator 28. For example, the anterior actuator 28 may define a pair of male ramps 90 proximate each end 82, 84 of the actuator 28 and configured to mate with the corresponding anterior ramps 72 along the side rails 44, 46 of the endplates 16, 18. The point contact pivoting ramp 90 may be configured to interface corresponding anterior ramp 72 at a singular contact point or location, facilitating pivoting or rotational movement. The singular location where the ramp 90 interacts with corresponding ramp 72 may be a focal point around which rotation or movement occurs. Unlike broad surface contact between mating ramps, ramp 90 may have targeted contact at a defined point or edge that interfaces with corresponding ramp 72. The engaging surface of the male ramp 90 may be pointed, angled, tapered, curved, etc. to define a single point or edge of contact.

In one embodiment, the male ramps 90 may include projections or protrusions with a rail configured to engage with the corresponding grooves or slots 74 in the endplates 16, 18. In some embodiments, the protrusions or rails may include L-shaped tabs which extends out from the actuator 28 and then make a 90-degree turn forming the L shape. In other embodiments, the protrusion or rails may include T-shaped tabs with a stem which extends out from the actuator 28 and then provides a perpendicular extension at the free end of the stem forming the top of the T shape. The free ends of the tabs may point laterally outward and away from one another or in any suitable manner. The slots 74 machined into the upper and lower endplates 16, 18 interface with the point contact pivoting ramps 90 on the anterior actuator 28 allowing for parallel and lordotic expansion, while preventing disassembly by pulling the endplates apart. Two limit pins 92 may thread into the anterior actuator 28 to prevent the implant 10 from being disassembled if over expanded. The point contact pivoting ramps 90 on the anterior actuator 24 translate axial motion from the actuator screw 22 into anterior expansion, and the ability of the endplate slots 74 to pivot about the point contact allows for independent expansion of the anterior and posterior actuators 28, 30.

The actuator assembly 20 includes a moveable posterior actuator 30 positioned between the upper and lower endplates 16, 18, thereby providing posterior expansion to the implant 10. The moveable posterior actuator 30 includes a laterally extending body connecting a first free end 102 to a second free end 104 with a flat anterior face 106 and an opposite posterior face 108. The first and second free ends 102, 104 are receivable between the upper and lower endplates 16, 18 toward the posterior end 12 of the implant 10. The posterior actuator 30 defines a central threaded cylindrical bore 110 configured to receive the actuator screw 22. The central axis of bore 110 may be aligned with the central longitudinal axis A of the implant 10. As best seen in FIG. 1B, in the collapsed position, the flat anterior face 106 may be configured to contact or rest against the posterior face of the central portion 80 of the anterior actuator 28.

The moveable posterior actuator 30 includes one or more ramps 112 configured to mate with corresponding ramps 70 on the endplates 16, 18. The ramps 112 may be defined into and/or extend from the posterior face 108 of the actuator 30. Similar to ramps 90, the ramps 112 may include a point contact pivoting ramp surface incorporated into each side of the moveable posterior actuator 30. For example, the moveable posterior actuator 30 may define a pair of male ramps 112 at each end 102, 104 of the actuator 28 and configured to mate with the posterior ramps 70 along the posterior rail 40 of the endplates 16, 18. Two male ramps 112 may be positioned upward to interface with the upper endplate 16 and two male ramps 112 may be positioned downward to interface with the lower endplate 18. The male ramps 112 may include projections or protrusions having a L-shaped tabs configured to engage with the corresponding grooves or slots 74 in the endplates 16, 18. The free ends of the L-shaped or T-shaped tabs may point laterally and away from one another on opposite sides 102, 104 of the actuator 30. The point contact pivoting ramps 112 on the moveable posterior actuator 30 interface with the corresponding slots 74 in the upper and lower endplates 16, 18, preventing disassembly and allowing for independent expansion.

The actuator assembly 20 includes a stationary posterior actuator 32 positioned between the upper and lower endplates 16, 18, thereby providing posterior expansion to the implant 10. The stationary posterior actuator 32 includes a laterally extending body having a first free end 120 and a second free end 122 on opposite sides. The first and second free ends 120, 122 are receivable between the posterior rails 40 of the upper and lower endplate 16, 18, and the stationary posterior actuator 32 defines the nose or front end 12 of the implant 10. The stationary posterior actuator 32 includes an anterior face 124 and an opposite posterior face 126. A central block 128 may protrude from the anterior face 124 which defines a central non-threaded bore 130 sized and dimensioned to receive the posterior actuator nut 26. The central axis of bore 130 may be aligned with the central longitudinal axis A of the implant 10.

The posterior expansion mechanism functions by using the actuator screw 22 to drive the moveable posterior actuator 30 toward the stationary posterior actuator 32. As best seen in FIG. 2B, the moveable posterior actuator 30 translates away from anterior actuator 28 and posteriorly toward stationary posterior actuator 32. As the two posterior actuators 30, 32 move toward one another, these posterior actuators 30, 32 interface with ramped surfaces 70 and slots 74 on the upper and lower endplates 16, 18, pushing the upper and lower endplates 16, 18 out in both directions, expanding the posterior height of the implant 10.

The stationary posterior actuator 32 includes one or more ramps 132 configured to mate with corresponding posterior ramps 70 on the endplates 16, 18. The ramps 132 may be defined into and/or extend from the anterior face 124 of the actuator 32. Similar to ramps 90, 112, the ramps 132 may include point contact pivoting ramp surfaces. For example, the posterior actuator 32 may define a male ramp 132 near each end 120, 122 of the actuator 32 configured to mate with the posterior ramps 70 along the posterior rails 40 of the endplates 16, 18. A pair of posterior ramps 132 may be positioned near each end 120, 122 with two configured to engage the upper endplate 16 and two configured to engage the lower endplate 18. The male ramps 132 may include projections or protrusions having a L-shaped or T-shaped tabs configured to engage with the corresponding grooves or slots 74 in the endplates 16, 18. The free ends of the tabs may point laterally and away from one another. When the moveable posterior actuator 30 moves toward the stationary posterior actuator 32, these posterior actuators 30, 32 interface with ramped surfaces 70 and slots 74 on the upper and lower endplates 16, 18, pushing the upper and lower endplate 16, 18 out in both directions, thereby expanding the posterior height of the implant 10.

Instead of accommodating lordotic angle adjustment by allowing the engagement features (e.g., T-slots and rails) to rotate about a set axial pivot point in the anterior and posterior actuators 28, 30, 32, implant 10 uses a point contact on the engagement interface itself as a pivot point for lordotic angle adjustment. The point contact engagement interface 90, 112, 132 includes enough angular clearance with the mating engagement slot 74 to accommodate the endplate angle change required for in-situ lordotic adjustment and device assembly.

The actuator assembly 20 includes actuator screw 22, anterior actuator nut 24, and posterior actuator nut 26 aligned along the central longitudinal axis A of the implant 10. The actuator screw 22 extends from a proximal end 140 to a distal end 142. The actuator screw 22 may include a shaft with external threads(s) or an exterior threaded portion 144 extending along its length. The threaded shaft 144 may have a given diameter, handedness, thread form, thread angle, lead, pitch, etc. suitable for interfacing with both the anterior actuator nut 24 and the moveable posterior actuator 30. In this embodiment, a single type of thread profile is used for both parallel and lordotic expansion. Other systems may require three different sets of threads to engage for parallel expansion. Conversely, threaded shaft 144 achieves parallel and lordotic expansion through the interaction of one set of threads. This reduces the overall increase in lifting torque created by friction or binding of the threads.

The proximal end 140 of shaft 22 may define an instrument recess 146 configured to receive an instrument, such as a driver, to rotate or actuate the actuator screw 22. The instrument recess 146 may include a tri-lobe, hex, star, or other suitable recess configured to engage with a driver instrument to apply torque to the actuator screw 22. The proximal end 140 of the shaft is configured to thread into the anterior actuator nut 24 to translate the moveable anterior actuator 28. The threaded shaft 144 also threads through the moveable posterior actuator 30 to translate the moveable posterior actuator 30 along central longitudinal axis A.

The distal end 142 of the actuator screw 22 may have a reduced distal tip, for example, having a diameter less than the diameter of the threaded shaft 144. The distal tip 142 may be threaded and configured to thread into the posterior actuator nut 26 retained in the stationary posterior actuator 32. Even at full expansion, for example shown in FIGS. 6A-6B, the distal end 142 of the actuator screw 22 does not protrude out past the posterior edge or front nose 12 of the implant 10 as may be seen in other designs. Posterior protrusion of the actuator screw was a point of concern from surgeons due to the optics of having the rod protruding near the posterior structures of the spine. Thus, the expansion assembly 20 and operation for implant 10 eliminates the possibility of any posterior protrusion of the actuator screw 22.

Figure 6A:
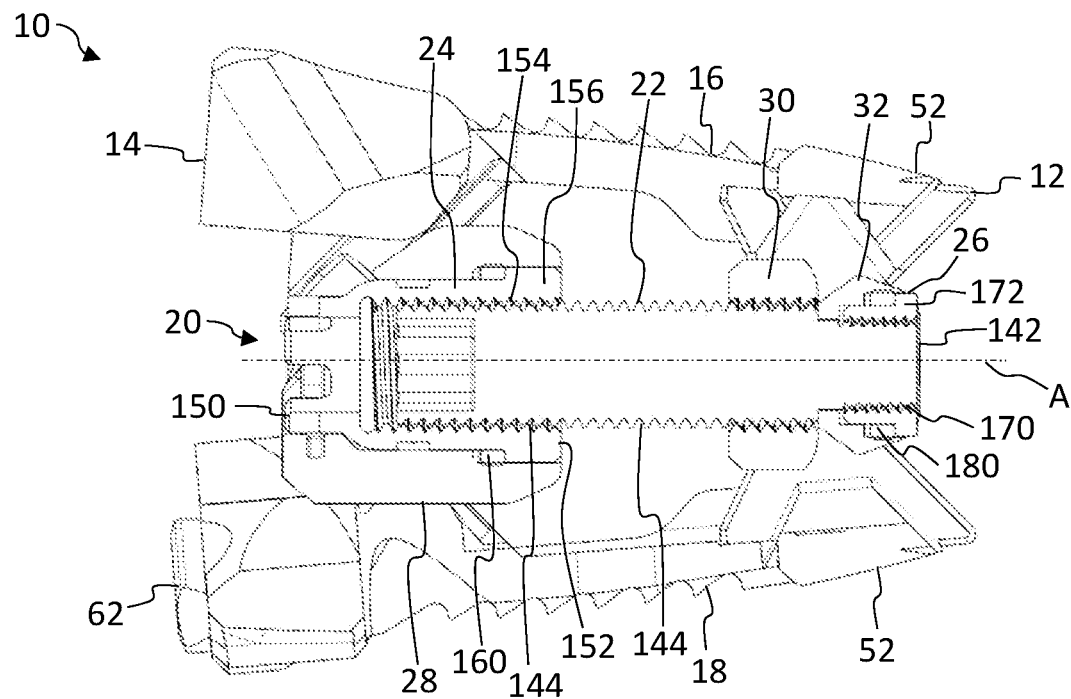
FIGS. 6A-6B illustrate vertical cross-sectional views of the expandable implant in the fully expanded position according to one embodiment.
Figure 6B:
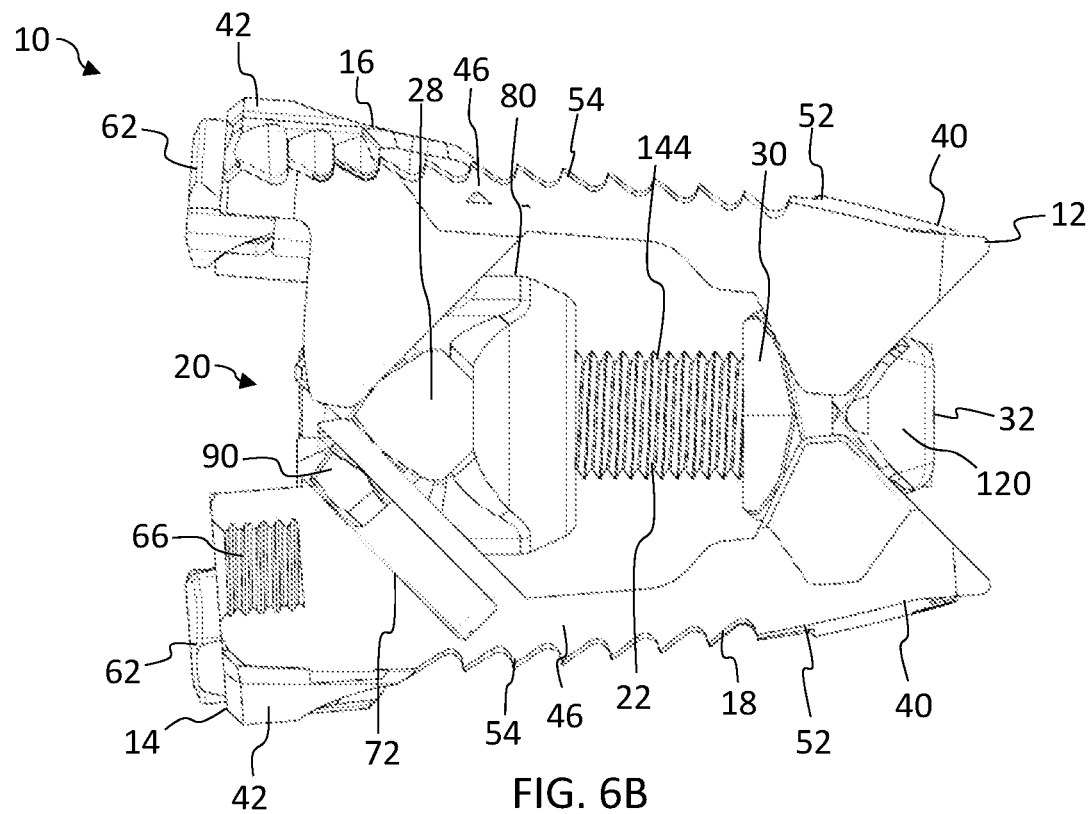
Figure 7:
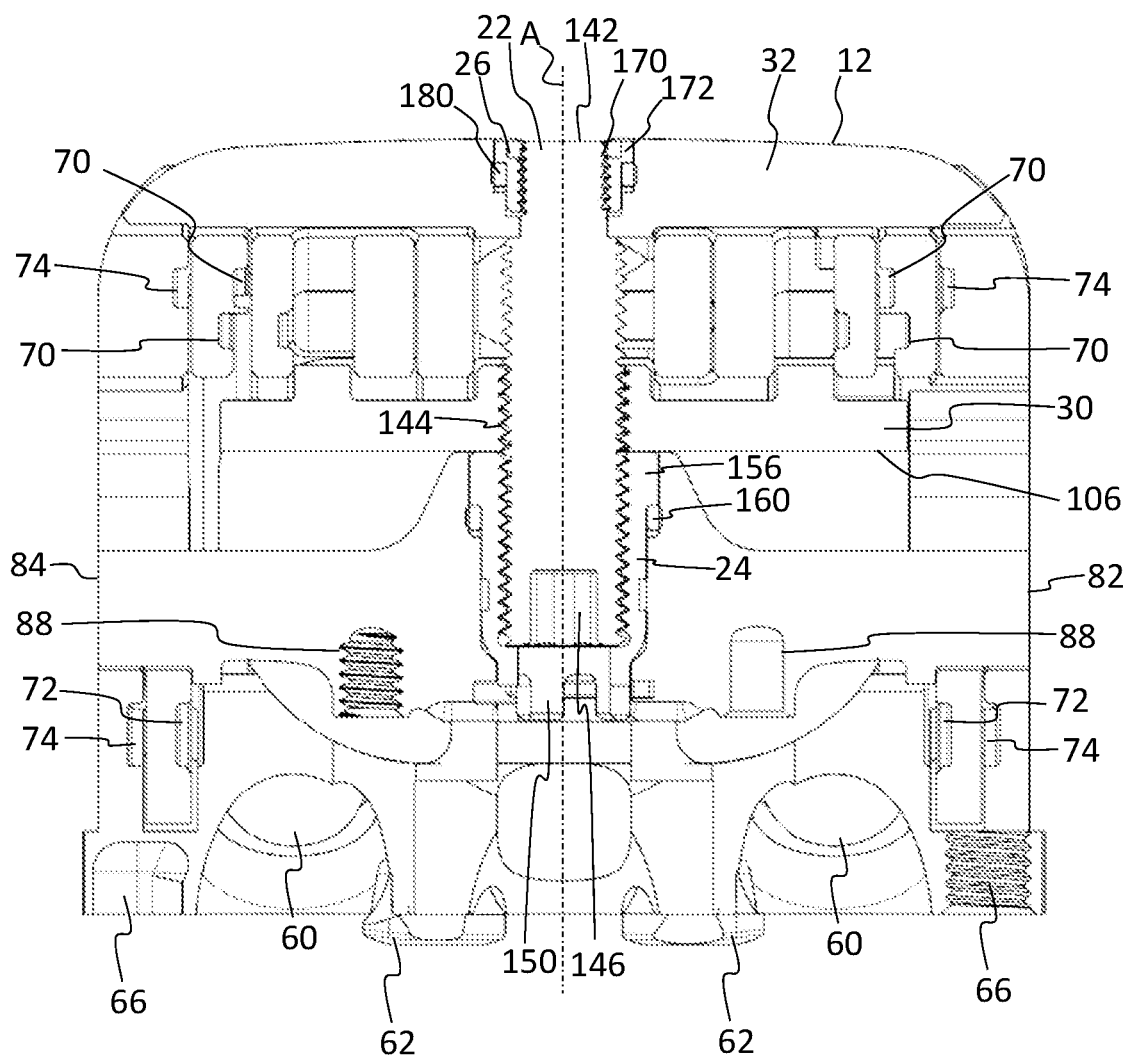
FIG. 7 shows an axial cross-sectional view of the expandable implant according to one embodiment.

The anterior actuator nut 24 has a body extending between a proximal end 150 to a distal end 152. As best seen in FIG. 6A, a central bore 154 extends through the body of the anterior actuator nut 24 from the proximal end 150 to the distal end 152. A portion of the bore 154 defines internal threads which are configured to threadably engage with the exterior threads 144 of the actuator screw 22. The proximal end 150 of the anterior actuator nut 24 defines a driver engagement recess, such as a series of notches and teeth or other suitable recess configured to engage with a driver instrument to apply torque to the anterior actuator nut 24. The driver recess for the anterior actuator nut 24 may be preferably different from the driver recess 146 for the actuator screw 22. The distal end 152 of the actuator nut 24 may have an enlarged collar 156. An anterior drag ring 160, such as a PEEK washer or annular ring, may be nested against the collar 156. The anterior drag ring 160 may be captured between the anterior actuator nut 24 and anterior actuator 28 to provide frictional resistance against back-driving the anterior expansion mechanism resulting in loss of anterior height of the implant. The anterior actuator nut 24 may be permanently captured inside the anterior actuator 28, for example, by two pins 162 or other suitable mechanism.

The posterior actuator nut 26 includes a body with a central cylindrical bore 170 defined therethrough. The bore 170 defines internal threads which are configured to threadably engage with the exterior threads of the distal tip 142 of the actuator screw 22. The actuator screw 22 is captured inside the stationary posterior actuator ramp 32 by threading into the posterior actuator nut 26. The end of the posterior actuator nut 26 may have an enlarged collar 172 such that a posterior drag ring 180 may be seated beneath the collar 172. The posterior drag ring 180, such as a PEEK washer or annular ring, is captured between the posterior actuator nut 26 and stationary posterior actuator ramp 32 to provide frictional resistance against back-driving the posterior expansion mechanism resulting in loss of overall expanded height of the implant 10. The drag rings 160, 180 may be added between the actuator screw 22 and the stationary posterior actuator 32 and between the anterior actuator 28 and anterior actuator nut 24 to ensure that neither the anterior or posterior actuators 28, 32 lose height during use.

During operation, the implant 10 may be operated in one of two modes. In a first mode, the actuator screw 22 and the anterior actuator nut 24 are rotated or turned together simultaneously. This moves the moveable posterior actuator 30 toward the stationary posterior actuator 32, forcing the upper and lower endplates 16, 18 apart. Because the ramp angle of the ramps 72 on the anterior end of the endplate 16, 18 match the ramp angle of the ramps 70 on the posterior end of the endplate 16, 18, this results in equal expansion of both endplates 16, 18. For example, FIGS. 2A-2B show the endplates 16, 18 expanded in a parallel manner. In a second mode, the actuator screw 22 is held in place and the anterior actuator nut 24 is rotated or turned alone. This makes the anterior actuator 28 move alone which expands or contracts the anterior end of each endplate only and results in an increase in lordotic angle. For example, FIGS. 3A-3B show the endplates 16, 18 expanded with an increased anterior height.

The expansion mechanism simplifies the expansion driver (not shown) because the actuator screw 22 and the anterior actuator nut 24 need to be turned in the same direction for both lordotic and parallel expansion. In other designs, the components 22, 24 are rotated in opposite directions, for example, if the actuator screw needed to be turned clockwise for parallel expansion, the anterior actuator nut needed to be turned counterclockwise for lordotic expansion. This required either counterintuitive counter-clockwise motion for implant expansion, or a complex and expensive driver mechanism. Conversely, in this embodiment, the actuator screw 22 and the anterior actuator nut 24 are rotated in the same direction for both lordotic and parallel expansion, thereby simplifying the operation.

The implant 10 allows for continuous expansion and distraction over the range of that specific implant. This provides the ability to distract vertebral bodies to a desired height, but also collapse the device 10 for repositioning if desired. The implant 10 has the ability for the endplates 16, 18 to converge providing lordosis, while maintaining a large window for bone graft placement. By changing lordotic angulation, the implant 10 may match the patient's natural lordosis or be used to provide a specific lordosis at the level(s) treated.

Turning now to FIGS. 8A-13B, an expandable fusion device or implant 210 is shown according to one embodiment. Implant 210 is similar to implant 10 with the addition of separate anterior and posterior pivot ramps 234, 236, 238. The expandable implant 210 extends along a central longitudinal axis A between front end or posterior end 212 and rear end or anterior end 214 of the device 210. The implant 210 includes upper and lower endplates 216, 218 configured to engage adjacent vertebrae, which define a height of the implant 210. The implant 210 includes an actuator assembly 220 configured for expanding the upper and lower endplates 216, 218.

The actuator assembly 220 includes a single actuator screw 222 threaded into anterior and posterior actuator ramps 228, 230 to independently control the anterior and posterior height of the implant. The implant 210 may include three separate actuators 228, 230, 232: a moveable anterior actuator 228, a moveable posterior actuator 230, and a stationary posterior actuator 232. One end of the actuator screw 222 threads into an anterior actuator nut 224 located in the moveable anterior actuator 228 and the opposite end of the actuator screw 222 threads into a posterior actuator nut 226 affixed to the stationary posterior actuator 232. The actuator screw 222 threads through the moveable posterior actuator 230 to translate the posterior actuator 230 along longitudinal axis A. The implant 210 also includes two anterior pivot ramps 234 slid onto each side of the anterior actuator 228, which interface with the upper and lower endplates 216, 218. The anterior pivot ramps 234 translate axial motion from the actuator screw 222 into anterior expansion, and pivot on the anterior actuator 228 to allow for independent expansion of the anterior and posterior actuators 228, 230, 232. The posterior expansion mechanism functions by using the actuator screw 222 to drive the moveable posterior actuator 230 toward the stationary posterior actuator 232. As these two components 230, 232 move toward one another, ramped surfaces 312, 332 push the posterior pivot ramps 236, 238 out in both directions, expanding the posterior height of the implant 210.

Figure 8A:
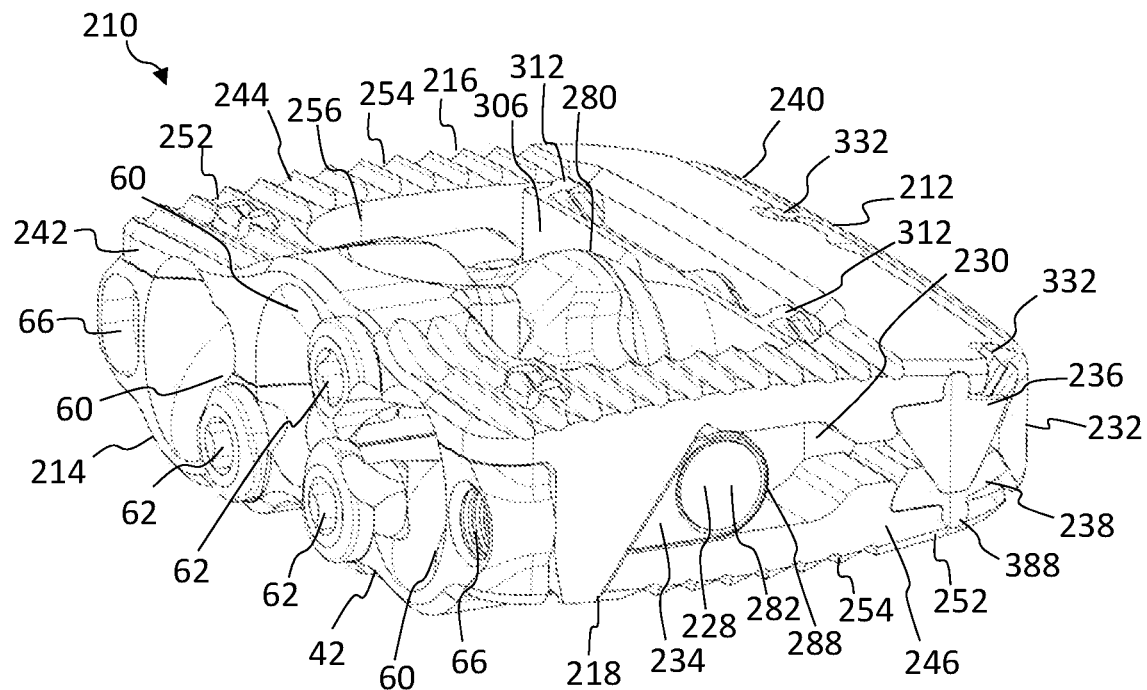
FIGS. 8A-8B illustrate perspective and side views, respectively, of an expandable implant in a collapsed position according to one embodiment.
Figure 8B:
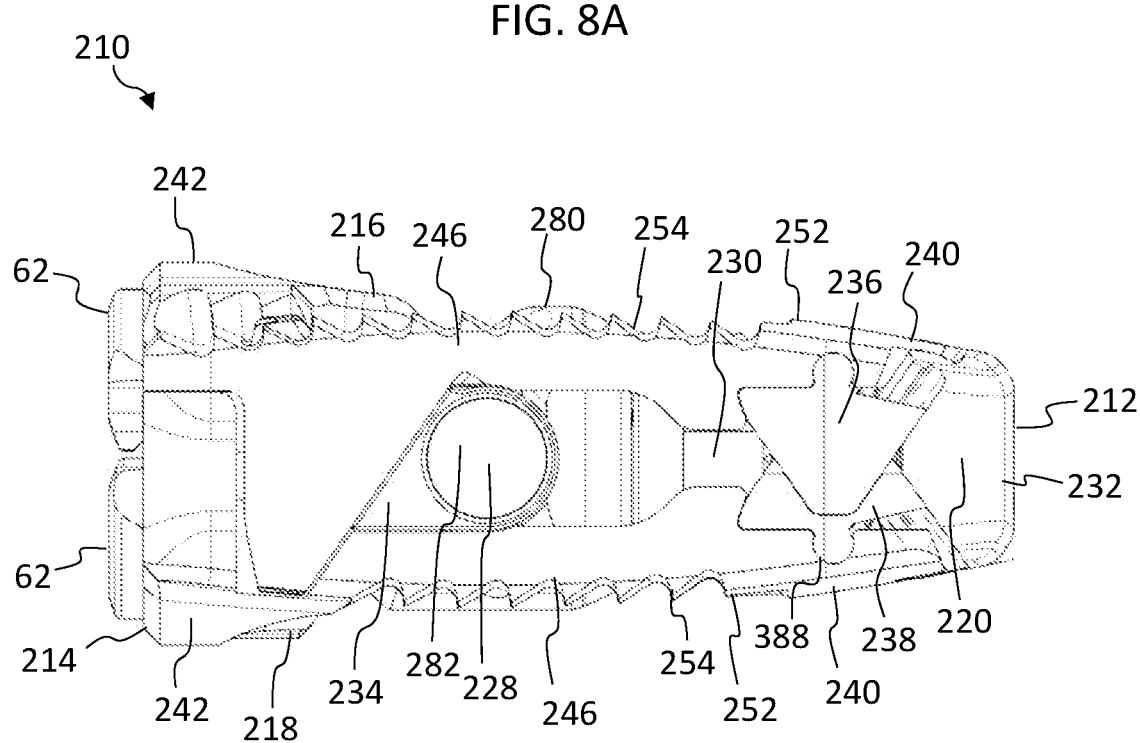
Figure 9A:
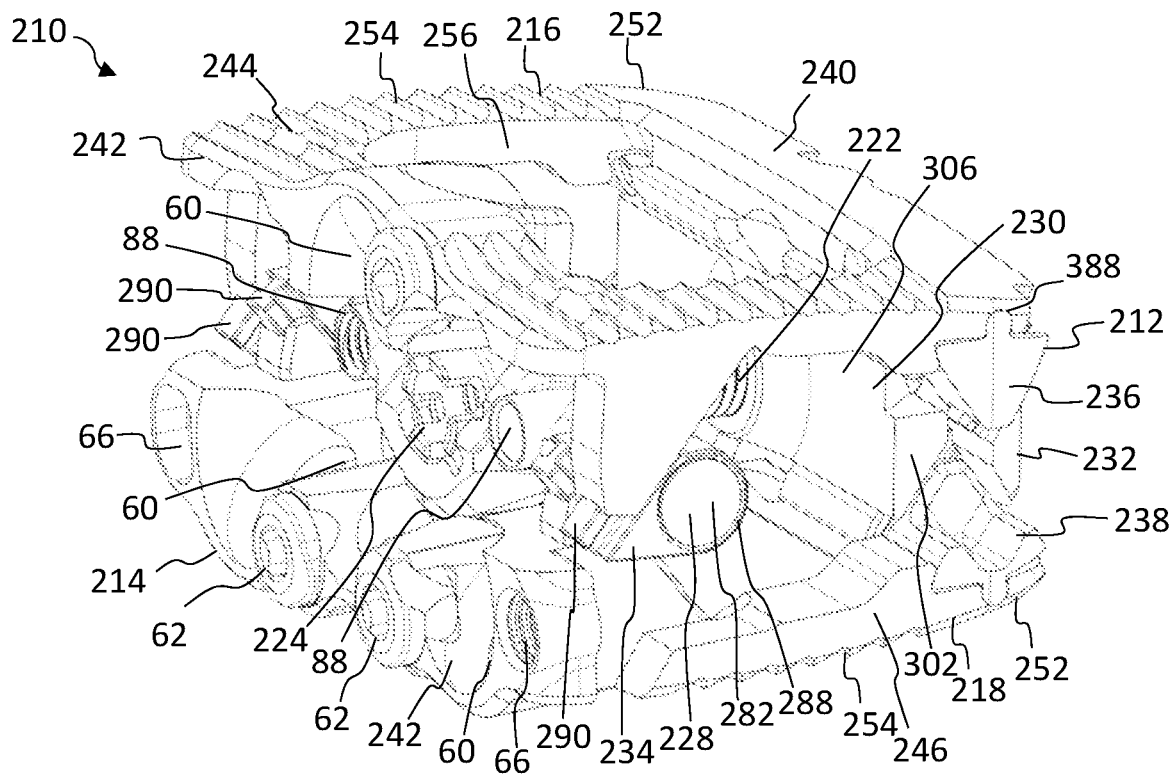
FIGS. 9A-9B illustrate perspective and side views, respectively, of the expandable implant in a fully expanded position according to one embodiment.
Figure 9B:
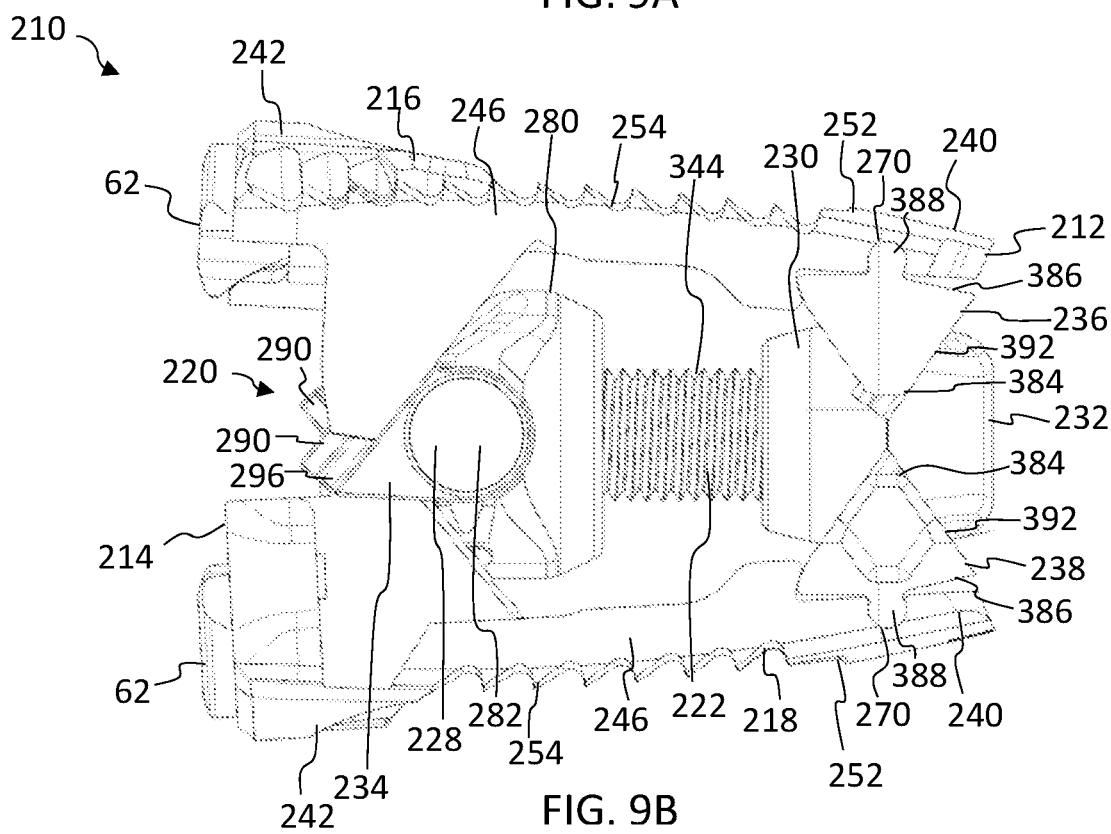
Figure 10A:
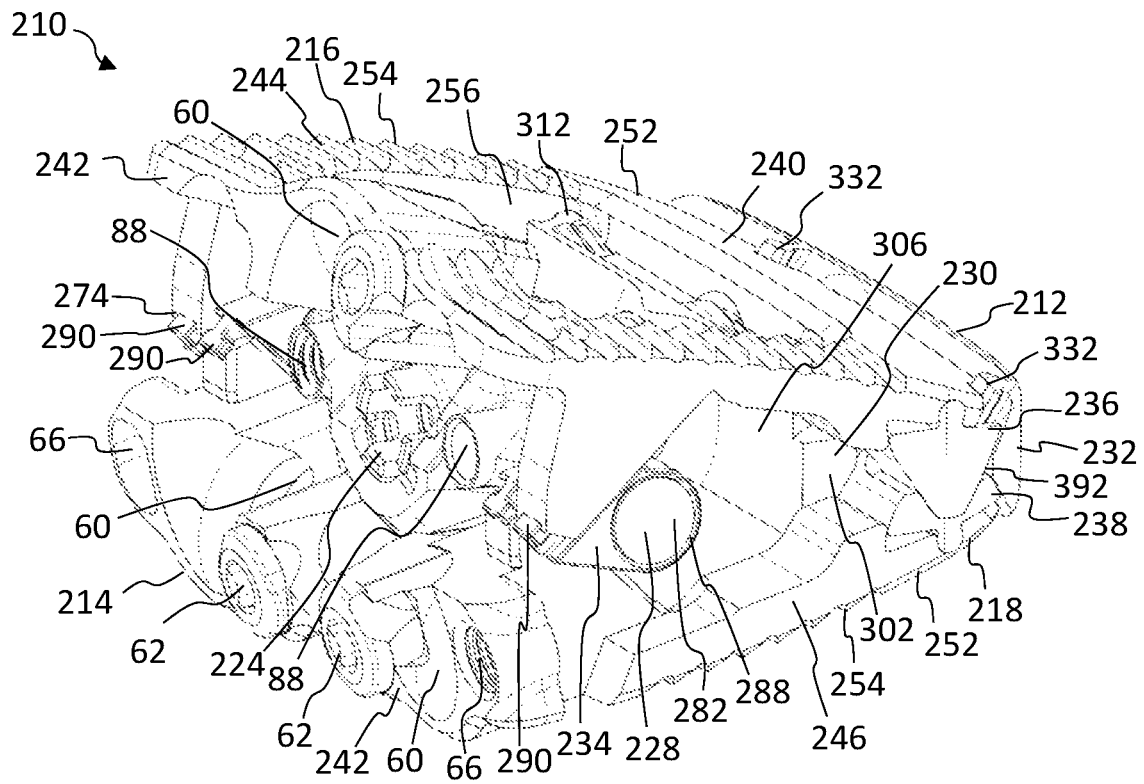
FIGS. 10A-10B illustrate perspective and side views, respectively, of the expandable implant in an expanded position with the anterior and posterior height of the implant independently controlled according to one embodiment.
Figure 10B:
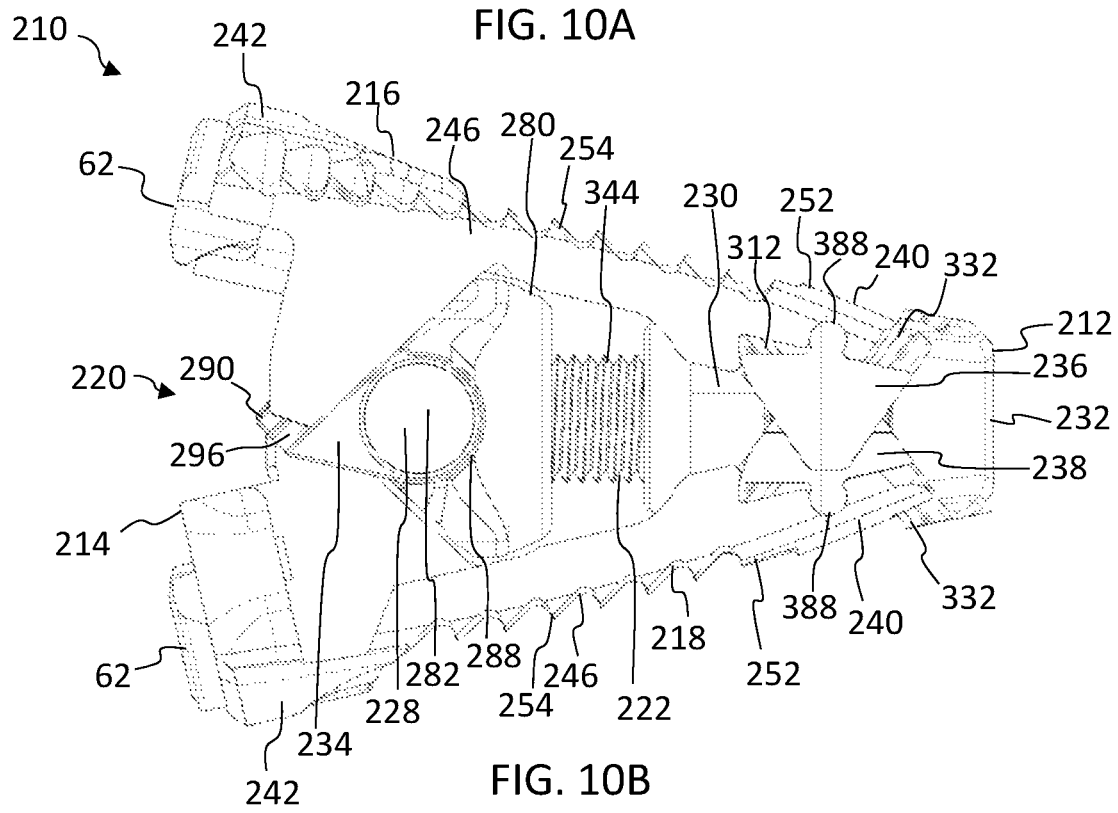
Figure 11:
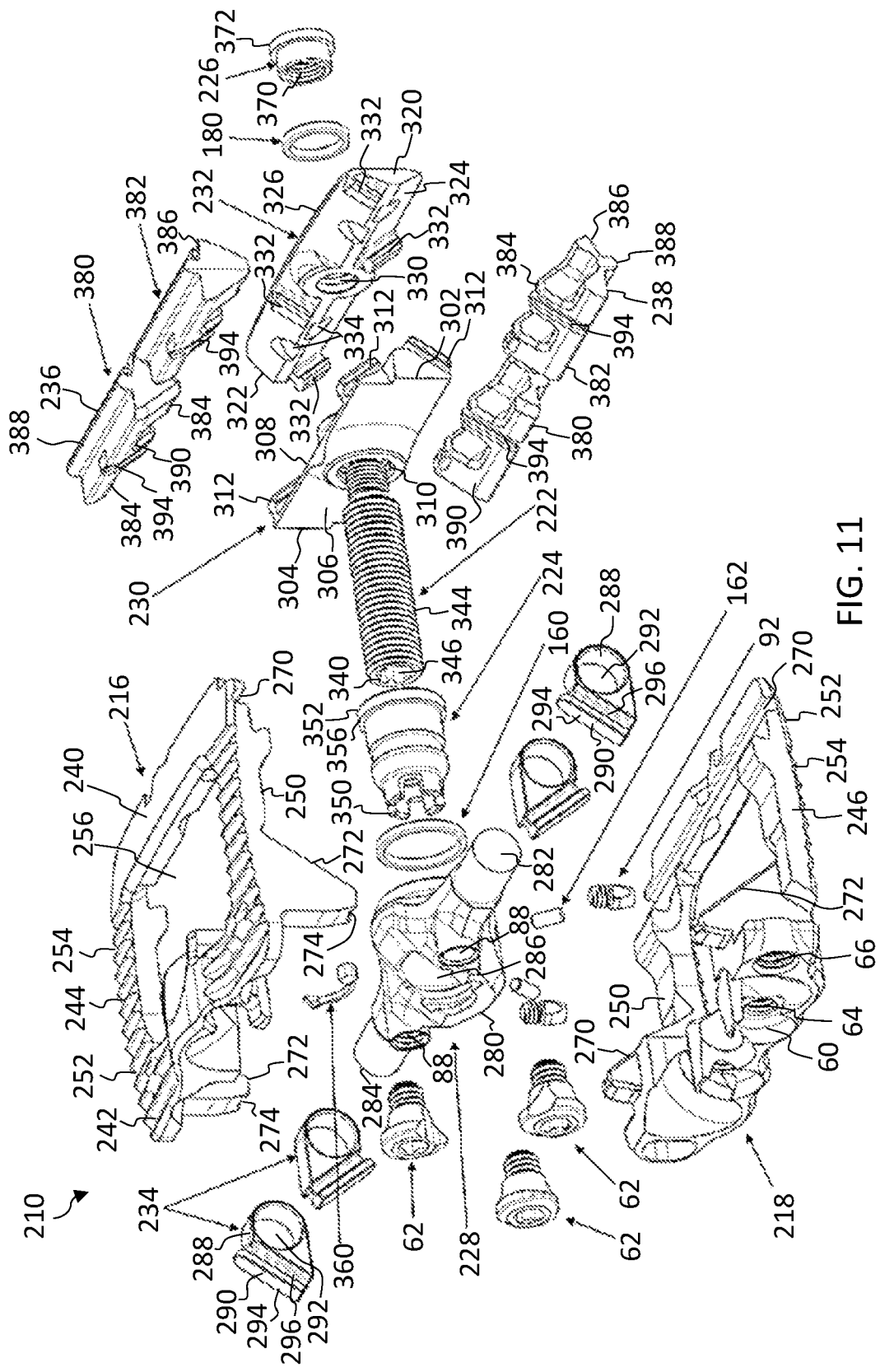
FIG. 11 illustrates an exploded view of the expandable implant according to one embodiment.
Figure 12A:
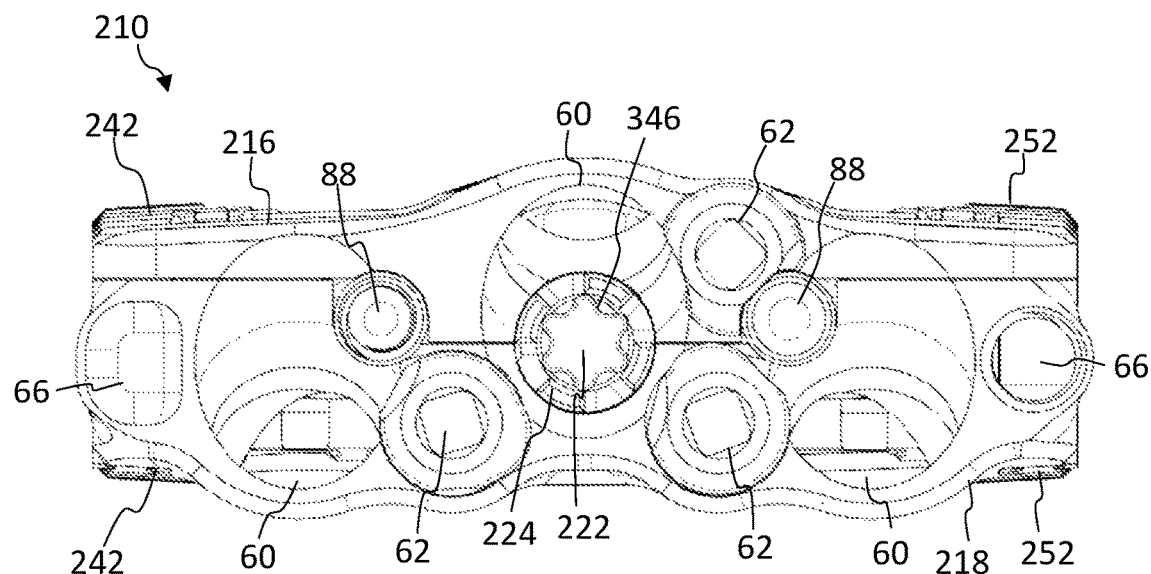
FIGS. 12A-12B illustrate anterior or rear views of the expandable implant in the collapsed and fully expanded positions, respectively, according to one embodiment.
Figure 12B:
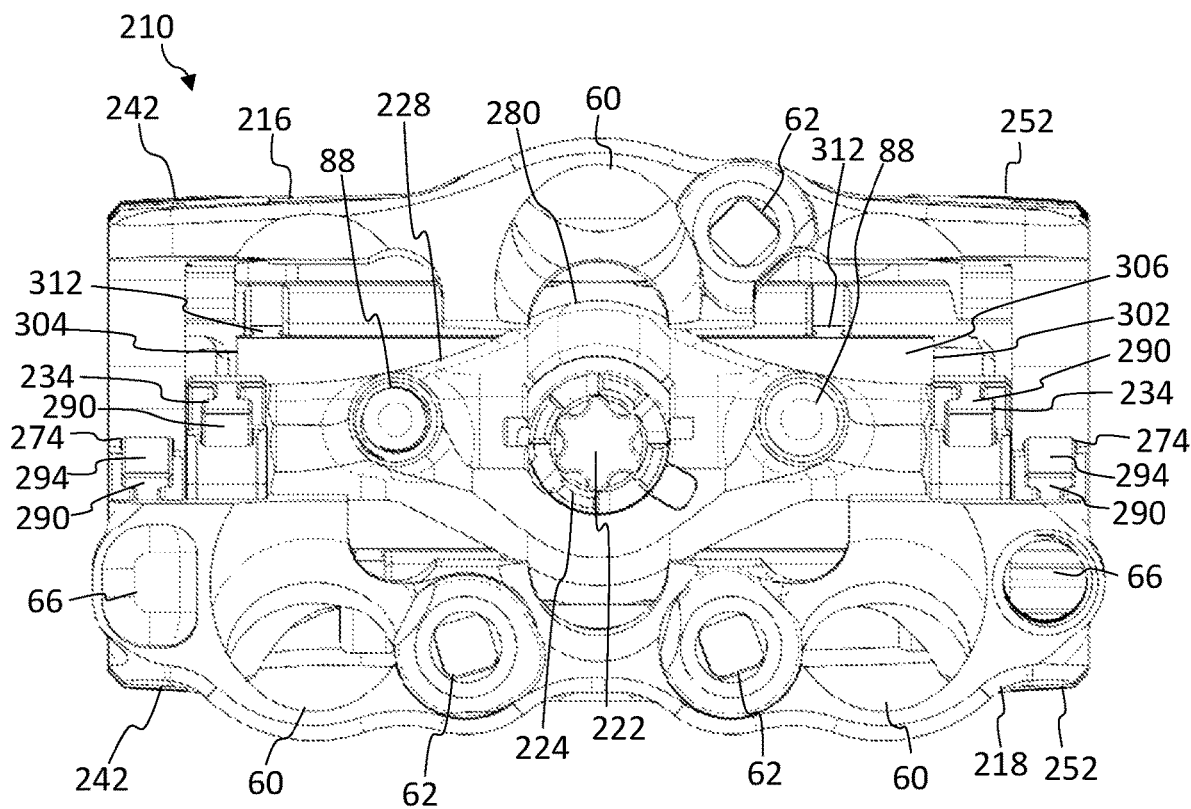

As best seen in FIGS. 8A-8B, the implant 210 is configured to be inserted into the disc space in a collapsed configuration. Once inserted into the disc space, the implant 210 is expanded in height to an expanded configuration to precisely restore spinal alignment and distribute load across the vertebral endplates. FIGS. 9A-9B show the implant 210 in a fully expanded configuration. FIGS. 10A-10B show the implant 210 in an expanded configuration where the anterior and posterior heights are independently adjustable to a desired lordotic profile. In this manner, the height is adjustable to restore height loss in the disc space and lordotic angulation.

Similar to endplates 16, 18, endplates 216, 218 include front or posterior rail 240 and rear or anterior rail 242 extending between opposed side rails 244, 246, which define an inner face 250 and an opposite outer face 252. The inner face 250 may be configured to mate with the pivot ramps 234, 236, 238 and the outer face 252 may be configured to contact adjacent vertebrae, for example, with teeth 254 or other friction increasing elements. Each endplate 216, 218 may define a vertical window or through passage 256 to define a central graft chamber configured to receive graft material or other therapeutic material.

In the same manner as implant 10, implant 210 may be secured to the adjacent vertebrae with one or more anchors or fixation screws (not shown) through respective anchor sockets 60. It will be appreciated that the sockets 60 may be present in any suitable number and configuration for fixation. In the alternative, the sockets 60 may be omitted to provide a standalone device. Cam style blocking screws 62 may be secured in blocking screw holes 64 in the endplates 216, 218, which block the anchors or fixation screws from migrating or backing out. In addition, the implant 210 may include one or more recesses or openings 66 for receiving an instrument, such as an insertion and/or expansion instrument.

The endplates 216, 218 are configured to expand via anterior pivot ramps 234 on the anterior or rear end 214 and posterior pivot ramps 236, 238 on the posterior or front end 212 of the implant 210. To accommodate the posterior pivot ramps 236, 238, the inner face 250 of each endplate 216, 218 may include a lateral groove or channel 270 configured to receive the posterior pivot ramps 236, 238 therein. The channel 270 may be positioned along the posterior rail 240 and defined into the inner face 250 of each endplate 216, 218. The channel 270 may be generally perpendicular to the longitudinal axis A of the implant 210. The channel 270 may have a rounded or curved profile to receive a corresponding protrusion or rib 388 from the posterior pivot ramps 236, 238. For example, the channel 270 may define a semicircular, hemispherical, parabolic, or other suitable cross-section.

Figure 13A:
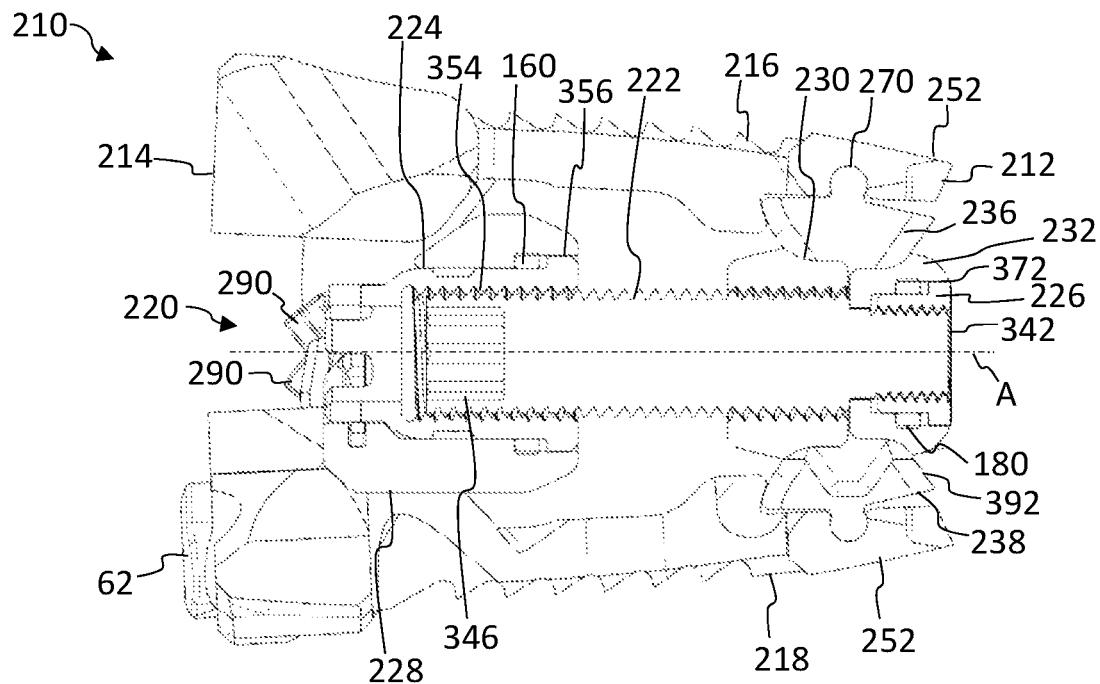
FIGS. 13A-13B show cross-sectional side and top views, respectively, of the expandable implant according to one embodiment.
Figure 13B:
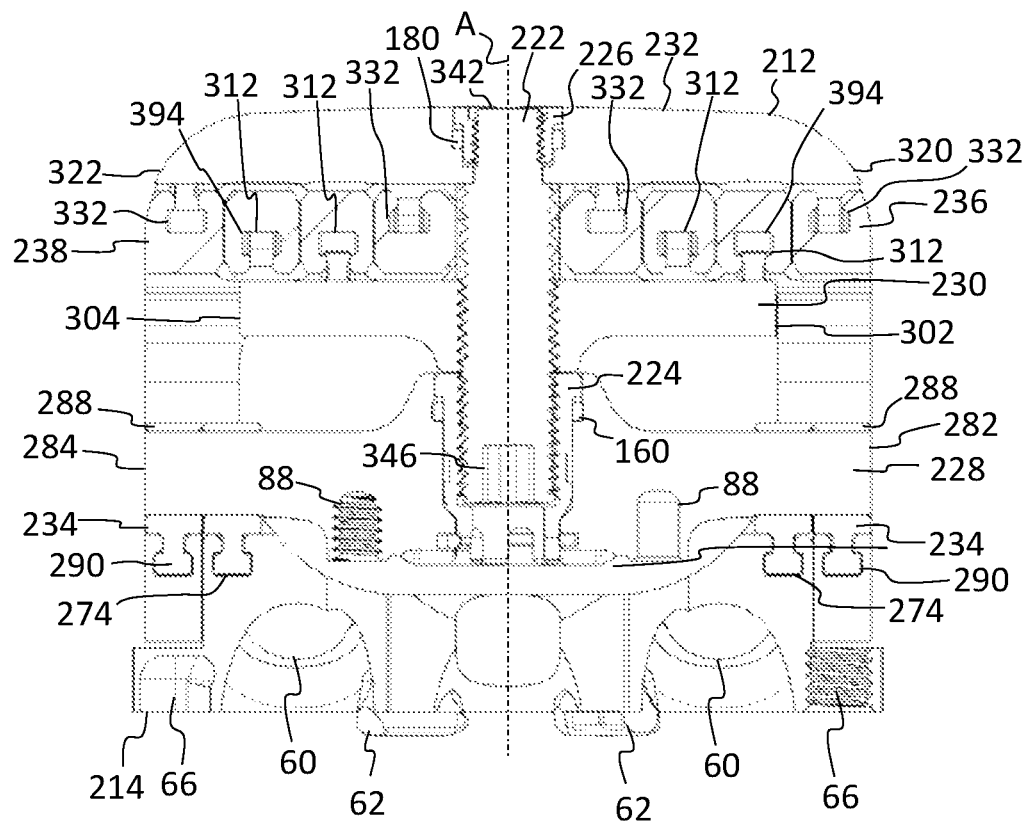

The anterior end 214 of each endplate 216, 218 may include one or more ramps 272 configured to mate with actuator 228, thereby causing the anterior end 214 of the endplates 216, 218 to separate apart. For example, the endplates 216, 218 may define anterior ramps 272 along the inner face 250 of the side rails 244, 246 toward the anterior end 214. The ramps 272 may include ramped surfaces, angled surfaces, or inclined planes with a given gradient or angle of slope. The ramps 272 may have generally straight ramped surfaces, may be curved, or may be configured in any suitable manner for slidable interface between the components. The ramps 272 may define male or female slide ramps configured to mate with corresponding ramps 294 on the anterior pivot ramps 234. As best seen in FIG. 13B, the ramps 272 on endplates 216, 218 include female ramps with grooves or slots 274 defined therein, such as T-slots. The groove or slots 274 may be configured to receive a portion of anterior pivot ramps 234, which pivot about actuator 228. The T-shaped engagement on these anterior pivot ramps 234 interface with the T-slots 274 on the upper and lower endplates 216, 218 and prevent disassembly. These anterior pivot ramps 234 translate axial motion from the actuator screw 222 into anterior expansion, and their ability to pivot on the anterior actuator 228 allows for independent expansion of the anterior and posterior actuators 228, 230, 232.

The actuator assembly 220 includes moveable anterior actuator 228 with anterior pivot ramps 234 positioned between the upper and lower endplates 216, 218, thereby providing anterior expansion to the implant 210. The moveable anterior actuator 228 includes a laterally extending body with an enlarged central portion 280. The anterior actuator 228 extends from a first free end 282 to a second free end 284. The first and second ends 282, 284 may each define a cylinder with a circular cross-sectional shape configured to receive the anterior pivot ramps 234. The first and second free ends 282, 284 are receivable between the side rails 244, 246 toward the anterior end 214 of the upper and lower endplates 216, 218 and the enlarged central portion 280 is positionable in the graft window 256 of the upper and lower endplates 216, 218 when in the collapsed configuration. The enlarged central portion 280 defines a central non-threaded bore 286 configured to receive the anterior actuator nut 224. The central axis of bore 286 may be aligned with the central longitudinal axis A of the implant 210. Similar to anterior actuator 28, additional recesses or bores 88 may be defined into the anterior actuator 228. For example, a first threaded bore 88 may be provided on one side of the central bore 286 and a second non-threaded bore 88 may be provided on the opposite side of the central bore 286, which are configured to attach an instrument, such as an insertion and/or expansion instrument to the anterior actuator 228. It will be appreciated that any suitable number, type, and configuration of instrument recesses may be used.

The moveable anterior actuator 228 supports one or more anterior pivot ramps 234 configured to mate with corresponding ramps 272 on the endplates 216, 218. Each anterior pivot ramp 234 may include a ring 288 and a foot 290. The ring 288 may be a full annular ring defining a central cylindrical through hole 292. The axis of through hole 292 may be aligned with a central lateral axis between ends 282, 284 of the anterior actuator 228. The ring 288 may have an outer surface and an inner surface configured to contact the anterior actuator 228. In particular, the cylindrical ends 282, 284 of anterior actuator 228 are positionable through the cylindrical through holes 292 of each anterior pivot ramps 234, thereby providing for pivotal movement about the anterior actuator 228. For example, two anterior pivot ramps 234 may be slid onto each cylindrical end 282, 284 of anterior actuator 228. The smooth inner surface of the anterior pivot ramps 234 allows each pivot ramp 234 to freely rotate on the corresponding smooth outer cylindrical surface of the anterior actuator 228.

The anterior pivot ramps 234 include foot 290 with a sliding surface 294 configured to mate with a corresponding sliding surface within groove 274 in the endplate 216, 218. The foot 290 may be a male projection extending away from one side of ring 288. The foot 290 may have a channel or groove 296 around its periphery, thereby forming the male projection, which is configured to enter the corresponding female recess 274 in the endplate 216, 218. The foot 290 may define an arched surface on one end and a planar surface on the opposite end. The sliding surface 294 may be a smooth flat or planar surface. The groove 296 may cause portions of the foot 290, including the arched end, to form an overhang. For example, the foot 290 may have a generally T-shaped cross section. The T-shaped foot 290 on the anterior pivot ramps 234 interface with the T-slots 274 on the upper and lower endplates 216, 218 and prevent disassembly.

The sliding surface 294 of each anterior pivot ramp 234 mates with the corresponding sliding surfaces within the grooves 274 in the endplates 216, 218 to allow for sliding motion between the components. For example, two pivot ramps 234 may be positioned on one end 282 of the anterior actuator 228: one configured to slidably engage the upper endplate 216 and one configured to slidably engage the lower endplate 218. Similarly, two pivot ramps 234 may be positioned on the opposite end 284 of the anterior actuator 228: one configured to slidably engage the upper endplate 216 and one configured to slidably engage the lower endplate 218. The anterior pivot ramps 234 are able to freely rotate on the cylindrical surfaces of the anterior actuator 228, which provides continuous contact between the sliding surfaces 294 of the anterior pivot ramps 234 and the endplates 216, 218 when the angulation between the endplates 216, 218 changes. The anterior pivot ramps 234 translate axial motion from the actuator screw 222 into anterior expansion, and their ability to pivot on the anterior actuator 228 allows for independent expansion of the anterior and posterior heights.

The actuator assembly 220 includes moveable posterior actuator 230 positioned between the upper and lower endplates 216, 218, thereby providing posterior expansion to the implant 210. The moveable posterior actuator 230 includes a laterally extending body connecting a first free end 302 to a second free end 304 with a flat anterior face 306 and an opposite posterior face 308. The first and second free ends 302, 304 are receivable between the upper and lower endplates 216, 218 toward the posterior end 212 of the implant 210. The posterior actuator 230 defines a central cylindrical threaded bore 310 configured to receive the actuator screw 222 therethrough. The central axis of bore 310 may be aligned with the central longitudinal axis A of the implant 210. A raised collar may be provided around bore 310 to reinforce the region surrounding the bore 310, thereby facilitating threaded engagement with the actuator screw 222 or additional strength to the posterior actuator 230.

The moveable posterior actuator 230 includes one or more ramps 312 configured to mate with corresponding ramps 394 on the posterior pivot ramps 236, 238. The ramps 312 may be defined into and/or extend from the posterior face 308 of the posterior actuator 230. The ramps 312 may include ramped surfaces, angled surfaces, or inclined planes with a given gradient or angle of slope. The ramps 312 may have generally straight ramped surfaces, may be curved, or may be configured in any suitable manner for slidable interface between the components. The ramps 312 may define male or female slide ramps configured to mate with corresponding ramps 394 on the posterior pivot ramps 236, 238. Similar to foot 290 on the anterior pivot ramps 234, the ramps 312 may include a sliding surface configured to mate with a corresponding sliding surface within groove 394 in the posterior pivot ramps 236, 238. The ramps 312 may be a male projection extending posteriorly. The ramps 312 may have a channel or groove around its periphery, thereby forming the male projection, which is configured to enter the corresponding female recess 394 in the posterior pivot ramps 236, 238. The ramps 312 may have a generally T-shaped cross section. The T-shaped ramps 312 on the moveable posterior actuator 230 interface with the T-slots 394 on the posterior pivot ramps 236, 238 and prevent disassembly and allow for independent expansion. Although a T-shaped interface is exemplified, it will be appreciated that other suitable slidable mating interfaces may also be used.

The actuator assembly 220 includes stationary posterior actuator 232, which defines the nose or front end 212 of the implant 210 and provides posterior expansion to the implant 210 using the posterior pivot ramps 236, 238. The stationary posterior actuator 232 includes a laterally extending body having a first free end 320 and a second free end 322 on opposite sides. The stationary posterior actuator 232 includes an anterior side 324 and an opposite posterior side 326. The anterior side 324 may be split into two angled faces: an upper portion tilted upward, and a lower portion tilted downward. The anterior side 324 defines a central non-threaded bore 330 configured to receive the posterior actuator nut 226. The central axis of bore 330 may be aligned with the central longitudinal axis A of the implant 210. A lateral spine with a central raised collar may be provided around bore 330 to reinforce the region surrounding the bore 330, thereby facilitating engagement with posterior actuator nut 226 or additional strength to the posterior actuator 232.

The stationary posterior actuator 232 includes one or more ramps 332 configured to mate with corresponding ramps 394 on posterior pivots ramps 236, 238. The ramps 332 may be defined into and/or extend from the anterior face 324 of the stationary posterior actuator 232. The ramps 332 may include ramped surfaces, angled surfaces, or inclined planes with a given gradient or angle of slope. The ramps 332 may have generally straight ramped surfaces, may be curved, or may be configured in any suitable manner for slidable interface between the components. The ramps 332 may define male or female slide ramps configured to mate with corresponding ramps 394 on the posterior pivot ramps 236, 238. Similar to ramps 312, the ramps 332 may include a sliding surface configured to mate with a corresponding sliding surface within groove 394 in the posterior pivot ramps 236, 238. The ramps 332 may be male projections extending anteriorly, with two ramps 332 extending upward from the upper angled face and two ramps 332 extending downward from the lower angled face. The ramps 332 may have a channel or groove around its periphery, thereby forming the male projection, which is configured to enter the corresponding female recess 394 in the posterior pivot ramps 236, 238. The ramps 332 may have a generally T-shaped cross section or other suitable shape, which interface with the T-slots 394 on the posterior pivot ramps 236, 238.

The stationary posterior actuator 232 may include one or more cutouts 334 configured to receive portions of the upper and lower posterior pivot ramps 236, 238 when the implant 10 is in its collapsed position. As shown in FIG. 8B, in the collapsed position, the anterior face 306 of the moveable posterior actuator 230 may contact or abut the posterior face of the anterior actuator 228. The posterior expansion mechanism functions by using the actuator screw 222 to drive the moveable posterior actuator 230 toward the stationary posterior actuator 232. FIG. 9B shows the moveable posterior actuator 230 separated from anterior actuator 228 and moved posteriorly toward stationary posterior actuator 232. As the two posterior actuators 230, 232 move toward one another, these actuators 230, 232 interface with ramped surfaces 394 on the posterior pivot ramps 236, 238, pushing the upper and lower endplates 216, 218 out in both directions, expanding the posterior height of the implant 210.

The upper and lower posterior pivot ramps 236, 238 may be the same or similar with mirrored and/or reversed positions. Each of the posterior pivot ramps 236, 238 may be separated into left and right sections 380, 382 positioned on opposite sides of the central actuator screw 222. Each section 380, 382 may include a laterally extending body configured to mate with the respective posterior actuators 230, 232 and the upper and lower endplates 216, 218. As best seen in FIG. 9B, the posterior pivot ramps 236, 238 may have a triangular or bell-shaped cross section with a narrower or tapered end 384 facing inward and a wider or flared end 386 facing outward. The flared end 386 has a lateral protrusion, lip, or rib 388 extending generally perpendicular to the longitudinal axis A of the implant 210. Each lateral rib 388 is receivable in the respective groove or channel 270 in the upper and lower endplates 216, 218. The lateral rib 388 may have a rounded or partially circular cross section configured to pivot in the respective channel 270. The circular rib 388 on the posterior pivot ramps 236, 238 interfaces with the corresponding cut 270 in the upper and lower endplates 216, 218 preventing disassembly and allowing for independent expansion of the anterior and posterior heights.

The upper and lower posterior pivot ramps 236, 238 have an anterior-facing side 390 and a posterior-facing side 392. The anterior-facing and posterior-facing sides 390, 392 may be slanted or sloped between the tapered end 384 and the flared end 386. The anterior-facing and posterior-facing sides 390, 392 define one or more ramps 394 configured to mate with the corresponding ramps 312, 332 on the posterior actuators 230, 232. The ramps 394 may be defined into and/or extend from the anterior-facing and posterior-facing sides 390, 392 of the posterior pivot ramps 236, 238. The ramps 394 may include ramped surfaces, angled surfaces, or inclined planes with a given gradient or angle of slope. The ramps 394 may have generally straight ramped surfaces, may be curved, or may be configured in any suitable manner for slidable interface between the components. Similar to ramps 272, the ramps 394 on posterior pivot ramps 236, 238 include female ramps with grooves or slots defined therein, such as T-slots. The T-shaped engagement on these posterior actuators 230, 232 interface with the T-slots 384 on the posterior pivot ramps 236, 238. As the moveable posterior actuator 230 moves toward the stationary posterior actuator 232, the ramped surfaces 312, 332, 394 push the left and right posterior pivot ramps 380, 382 out in both directions, expanding the posterior height of the implant 210.

The actuator assembly 220 includes actuator screw 222, anterior actuator nut 224, and posterior actuator nut 226 aligned along the central longitudinal axis A of the implant 210. The actuator screw 222 extends from a proximal end 340 to a distal end 342. The actuator screw 222 may include a shaft with an exterior threaded portion 344 extending along its length. The threaded shaft 344 may have a given diameter, handedness, thread form, thread angle, lead, pitch, etc. suitable for interfacing with both the anterior actuator nut 224 and the moveable posterior actuator 230. In this embodiment, a single type of thread profile is used for both parallel and lordotic expansion. Other systems may require three different sets of threads to engage for parallel expansion. Conversely, threaded shaft 344 achieves parallel and lordotic expansion through the interaction of one set of threads. This reduces the overall increase in lifting torque created by friction or binding of the threads.

The proximal end 340 may define an instrument recess 346 configured to receive an instrument, such as a driver, to rotate or actuate the actuator screw 222. The instrument recess 346 may include a tri-lobe, hex, star, or other suitable recess configured to engage with a driver instrument to apply torque to the actuator screw 222. The proximal end 340 of the shaft is configured to thread into the anterior actuator nut 224 to translate the moveable anterior actuator 228. The threaded shaft 344 also threads through the moveable posterior actuator 230 to translate the moveable posterior actuator 230.

The distal end 342 of the actuator screw 222 may have a reduced distal tip, for example, having a diameter less than the diameter of the threaded shaft 344. The distal tip 342 may be threaded and configured to thread into the posterior actuator nut 226. Even at full expansion, for example shown in FIGS. 9A-9B, the distal end 342 of the actuator screw 222 does not protrude out past the posterior edge or front nose 212 of the implant 210 as may be seen in other designs. Posterior protrusion of the actuator screw was a point of concern from surgeons due to the optics of having the rod protruding near the posterior structures of the spine. Thus, the expansion assembly 220 for implant 210 eliminates the possibility of any posterior protrusion of the actuator screw 222.

The anterior actuator nut 224 has a body extending between a proximal end 350 to a distal end 352. As best seen in FIG. 13A, a central bore 354 extends through the body of the anterior actuator nut 224 from the proximal end 350 to the distal end 352. A portion of the bore 354 defines internal threads which are configured to threadably engage with the exterior threads 344 of the actuator screw 222. The proximal end 350 of the anterior actuator nut 224 defines a driver engagement recess, such as a series of notches and teeth or other suitable recess configured to engage with a driver instrument to apply torque to the anterior actuator nut 224.

The distal end 352 of the actuator nut 224 may have an enlarged collar 356. Similar to implant 10, an anterior drag ring 160, such as a PEEK washer or annular ring, may be nested against the underside of the collar 356. The anterior drag ring 160 may be captured between the anterior actuator nut 224 and anterior actuator 228 to provide frictional resistance against back-driving the anterior expansion mechanism, which could result in loss of anterior height of the implant. The anterior actuator nut 224 may be permanently captured inside the anterior actuator 228, for example, by two pins 162 or other suitable mechanism. Additionally, a mechanical lock 360 may sit in the anterior actuator 228 and interface with the teeth of the anterior actuator nut 224 to provide additional security against loss of height of the implant 210.

The posterior actuator nut 226 includes a body with a central cylindrical bore 370 defined therethrough. The bore 370 defines internal threads which are configured to threadably engage with the exterior threads of the distal tip 342 of the actuator screw 222. The actuator screw 222 is captured inside the stationary posterior actuator ramp 232 by threading into the posterior actuator nut 226. The end of the posterior actuator nut 226 may have an enlarged collar 372 such that posterior drag ring 180 may be seated beneath the collar 372. Similar to implant 10, the posterior drag ring 180, such as a PEEK washer or annular ring, is captured between the posterior actuator nut 226 and stationary posterior actuator ramp 232. The drag ring 180 may provide frictional resistance against back-driving the posterior expansion mechanism resulting in loss of overall expanded height of the implant 210.

During operation, the implant 210 may be operated in one of two modes. In a first mode, the actuator screw 222 and the anterior actuator nut 224 are rotated and turned together at the same time. This moves the moveable posterior actuator 230 posteriorly toward the stationary posterior actuator 232, forcing the posterior pivot ramps 236, 238 upward. This results in equal, parallel expansion of both endplates 216, 218. In a second mode, the actuator screw 222 is not turned and the anterior actuator nut 224 is rotated or turned by itself. This makes the anterior actuator 228 move alone, which expands the anterior end of each endplate 216, 218 only and results in an increase in lordotic angle.

Similar to implant 10, implant 210 allows continuous expansion and distraction over the range of that specific implant. The vertebral bodies may be distracted to a desired height and the implant may be collapsed for repositioning, if desired. During expansion, the implant endplates may be expanded in parallel or may converge to provide lordosis, while maintaining a large window for bone graft placement. By changing lordotic angulation, the implant may be expanded to match the patient's natural lordosis or used to provide a specific lordosis at the level(s) treated.

Although the invention has been described in detail and with reference to specific embodiments, it will be apparent to one skilled in the art that various changes and modifications can be made without departing from the spirit and scope of the invention. Thus, it is intended that the invention covers the modifications and variations of this invention provided they come within the scope of the appended claims and their equivalents. It is expressly intended, for example, that all components of the various devices disclosed above may be combined or modified in any suitable configuration.

What is claimed is:

1. An expandable implant comprising:
   an upper endplate and a lower endplate configured to engage adjacent vertebrae; and an actuator assembly extending along a longitudinal axis of the implant and positioned between the upper and lower endplates for expanding the upper and lower endplates to independently control anterior and posterior heights of the implant, the actuator assembly including a moveable anterior actuator, a moveable posterior actuator, a stationary posterior actuator, an actuator screw threaded into an anterior actuator nut located in the moveable anterior actuator, and a posterior actuator nut located in the stationary posterior actuator, wherein the actuator screw threads through the moveable posterior actuator to translate the moveable posterior actuator, wherein the upper and lower endplates each define a plurality of ramps configured to mate with corresponding male protrusions on the moveable anterior actuator and the moveable and stationary posterior actuators, wherein the male protrusions on the moveable anterior actuator and the moveable and stationary posterior actuators include point contact pivoting ramps defined thereon which act as a pivot point, facilitating pivoting or rotational movement for a lordotic angle adjustment between the upper and lower endplates, wherein when the actuator screw and the anterior actuator nut are turned together, the moveable posterior actuator moves toward the stationary posterior actuator, forcing the upper and lower endplates apart resulting in parallel expansion, and when only the anterior actuator nut is turned, the moveable anterior actuator moves alone to increase the anterior height, resulting in an increase in a lordotic angle of the implant.

2. The expandable implant of claim 1, wherein the ramps on the upper and lower endplates include female T-slots.

3. The expandable implant of claim 1, wherein the moveable anterior actuator includes a laterally extending body with an enlarged central portion defining a non-threaded bore and opposing free ends defining an irregular cross-sectional shape.

4. The expandable implant of claim 1, wherein the moveable posterior actuator includes a laterally extending body defining a threaded bore with a flat anterior face and an opposite posterior face.

5. The expandable implant of claim 1, wherein the stationary posterior actuator includes a laterally extending body defining a non-threaded bore with an anterior face.

6. The expandable implant of claim 1, wherein the actuator screw includes a shaft having a single type of thread profile along its length and a reduced diameter at its distal end for threading into the posterior actuator nut, wherein the single type of thread profile is used to achieves both parallel and lordotic expansion.

7. An expandable implant comprising:
an upper endplate and a lower endplate configured to engage adjacent vertebrae; and
an actuator assembly extending along a longitudinal axis of the implant and positioned between the upper and lower endplates for expanding the upper and lower endplates to independently control anterior and posterior heights of the implant, the actuator assembly including a moveable anterior actuator receiving and securing a plurality of anterior pivot ramps, a moveable posterior actuator, a stationary posterior actuator engaged with upper and lower posterior pivot ramps, and an actuator screw threaded into an anterior actuator nut located in the moveable anterior actuator, and a posterior actuator nut located in the stationary posterior actuator, wherein the actuator screw threads through the moveable posterior actuator to translate the moveable posterior actuator, wherein each anterior pivot ramp has a smooth inner surface to allow each anterior pivot ramp to rotate on the moveable anterior actuator, wherein the upper and lower endplates each define a plurality of ramps configured to mate with corresponding ramped surfaces on the anterior pivot ramps and the upper and lower posterior pivot ramps, wherein when the actuator screw and the anterior actuator nut are turned together, the moveable posterior actuator moves toward the stationary posterior actuator, forcing the upper and lower posterior pivot ramps outward resulting in parallel expansion of the upper and lower endplates, and when only the anterior actuator nut is turned, the moveable anterior actuator moves alone to increase the anterior height, resulting in an increase in a lordotic angle of the implant.

8. The expandable implant of claim 7, wherein each anterior pivot ramp has a ring received on the moveable anterior actuator and a foot comprising the ramped surface configured to mate with the respective ramps on the upper and lower endplates.

9. The expandable implant of claim 8, wherein each foot is a male projection extending from one side of the ring, and each ramp on the upper and lower endplates is female recess configured to receive the respective male projection of the foot.

10. The expandable implant of claim 8, wherein the moveable anterior actuator includes a laterally extending body with an enlarged central portion defining a non-threaded bore and opposing free ends defining cylindrical ends.

11. The expandable implant of claim 10, wherein each anterior pivot ramp is configured to rotate on the cylindrical ends of the moveable anterior actuator.

12. The expandable implant of claim 7, wherein the upper and lower posterior pivot ramps each include left and right sections positioned on opposite sides of the actuator screw.

13. The expandable implant of claim 7, wherein the upper and lower posterior pivot ramps each include a laterally extending body with a bell-shaped cross section having a tapered end and a flared end.

14. The expandable implant of claim 13, wherein the flared end of the upper and lower posterior pivot ramps includes a lateral rib having a circular cross section configured to pivot in a corresponding channel in the upper and lower endplates.

15. A method of spinal fixation comprising:
inserting an expandable intervertebral implant into a disc space between adjacent vertebrae, the expandable implant comprising upper and lower endplates each configured to engage one of the adjacent vertebrae and an actuator assembly extending along a longitudinal axis of the implant and positioned between the upper and lower endplates for expanding the upper and lower endplates to independently control anterior and posterior heights of the implant, the actuator assembly including a moveable anterior actuator, a moveable posterior actuator, a stationary posterior actuator, an actuator screw threaded into an anterior actuator nut located in the moveable anterior actuator, and a posterior actuator nut located in the stationary posterior actuator, wherein the actuator screw threads through the moveable posterior actuator to translate the moveable posterior actuator, wherein the upper and lower endplates each define a plurality of ramps configured to mate with corresponding male protrusions on the moveable anterior actuator and the moveable and stationary posterior actuators, wherein the male protrusions on the moveable anterior actuator and the moveable and stationary posterior actuators include point contact pivoting ramps defined thereon which act as a pivot point, facilitating pivoting or rotational movement for a lordotic angle adjustment between the upper and lower endplates;

and expanding the implant in height by:

(1) rotating the actuator screw and the anterior actuator nut together to move the moveable posterior actuator toward the stationary posterior actuator, thereby forcing the upper and lower endplates apart resulting in parallel expansion; or (2) rotating only the anterior actuator nut to move the moveable anterior actuator alone to increase the anterior height, resulting in an increase in a lordotic angle of the implant.

16. The method of claim 15, further comprising inserting bone anchors through sockets in the upper and lower endplates and into the adjacent vertebrae.

17. The method of claim 16, further comprising inserting blocking screws through holes in the upper and lower endplates and rotating the blocking screws in the upper and lower endplates to cover the bone anchors and prevent the bone anchors from backing out.

* * * * *